US008715881B2

(12) United States Patent
Choi et al.

(10) Patent No.: US 8,715,881 B2
(45) Date of Patent: May 6, 2014

(54) BENZOXAZINE-BASED MONOMER, POLYMER THEREOF, ELECTRODE FOR FUEL CELL INCLUDING THE SAME, ELECTROLYTE MEMBRANE FOR FUEL CELL INCLUDING THE SAME, AND FUEL CELL USING THE SAME

(75) Inventors: Seongwoo Choi, Yongin-si (KR); Jungock Park, Yongin-si (KR); Wonmok Lee, Yongin-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 0 days.

(21) Appl. No.: 13/560,321

(22) Filed: Jul. 27, 2012

(65) Prior Publication Data
US 2012/0295181 A1    Nov. 22, 2012

Related U.S. Application Data

(62) Division of application No. 12/208,664, filed on Sep. 11, 2008, now Pat. No. 8,252,890.

(30) Foreign Application Priority Data

Sep. 11, 2007  (KR) .................. 10-2007-0092146

(51) Int. Cl.
H01M 2/16 (2006.01)
H01M 4/60 (2006.01)
H01M 4/86 (2006.01)
H01M 4/92 (2006.01)
H01M 8/10 (2006.01)

(52) U.S. Cl.
USPC ........... 429/483; 429/492; 429/516; 429/524; 429/530; 252/182.1; 528/403

(58) Field of Classification Search
None
See application file for complete search history.

(56) References Cited

U.S. PATENT DOCUMENTS

| | | | |
|---|---|---|---|
| 4,828,699 A | 5/1989 | Soehngen | |
| 5,098,985 A | 3/1992 | Harris et al. | |
| 5,250,633 A | 10/1993 | Calundann et al. | |
| 5,410,012 A | 4/1995 | Connell et al. | |
| 5,637,670 A | 6/1997 | Connell et al. | |
| 5,945,233 A | 8/1999 | Onorato et al. | |
| 6,042,968 A | 3/2000 | Onorato et al. | |
| 6,482,946 B1 | 11/2002 | Dettloff et al. | |
| 6,620,905 B1 | 9/2003 | Musa | |
| 6,855,674 B2 | 2/2005 | Gutierrez | |
| 7,094,490 B2 | 8/2006 | Cao et al. | |
| 7,157,509 B2 | 1/2007 | Li et al. | |
| 7,371,480 B2 | 5/2008 | Ono et al. | |
| 7,388,035 B2 | 6/2008 | Kim et al. | |
| 7,405,021 B2 | 7/2008 | Gascoyne et al. | |
| 7,510,678 B2 | 3/2009 | Kim et al. | |
| 7,619,044 B2 | 11/2009 | Lee et al. | |
| 7,649,025 B2 | 1/2010 | Kitamura et al. | |
| 7,709,579 B2 | 5/2010 | Lehmann et al. | |
| 2001/0041283 A1 | 11/2001 | Hitomi | |
| 2002/0127474 A1 | 9/2002 | Fleischer et al. | |
| 2002/0164516 A1 | 11/2002 | Hasegawa et al. | |
| 2003/0190516 A1 | 10/2003 | Tanno | |
| 2004/0005493 A1 | 1/2004 | Tanno | |
| 2004/0028976 A1 | 2/2004 | Cabasso et al. | |
| 2004/0206953 A1 | 10/2004 | Morena et al. | |
| 2004/0231143 A1 | 11/2004 | Visco et al. | |
| 2004/0241522 A1 | 12/2004 | Ono et al. | |
| 2004/0261660 A1 | 12/2004 | Li et al. | |
| 2005/0074651 A1 | 4/2005 | Kidai et al. | |
| 2005/0084728 A1 | 4/2005 | Kim et al. | |
| 2005/0089744 A1 | 4/2005 | Kim et al. | |
| 2005/0130006 A1 | 6/2005 | Hoshi et al. | |
| 2005/0142413 A1 | 6/2005 | Kimura et al. | |
| 2005/0247908 A1 | 11/2005 | Keller et al. | |
| 2006/0078774 A1 | 4/2006 | Uensal et al. | |
| 2006/0241192 A1 | 10/2006 | Kitamura et al. | |
| 2007/0020507 A1 | 1/2007 | Kim et al. | |
| 2007/0141426 A1 | 6/2007 | Choi et al. | |
| 2007/0184323 A1 | 8/2007 | Lee et al. | |
| 2007/0200994 A1 | 8/2007 | Yanagisawa | |
| 2007/0238723 A1 | 10/2007 | Goble et al. | |
| 2007/0275285 A1 | 11/2007 | Choi et al. | |
| 2008/0020264 A1 | 1/2008 | Sun et al. | |
| 2008/0045688 A1 | 2/2008 | Lin et al. | |
| 2008/0050633 A1 | 2/2008 | Kwon et al. | |
| 2008/0118817 A1 | 5/2008 | Lee et al. | |
| 2008/0145743 A1 | 6/2008 | Choi et al. | |

(Continued)

FOREIGN PATENT DOCUMENTS

CN    101220153    7/2008
DE    2034 887     1/1972

(Continued)

OTHER PUBLICATIONS

Toyama et al., Chem. Pharm. Bull., vol. 22, No. 12, pp. 5543-6 (1985).*
STN Registry Database entry for CAS RN 35141-82-3, Published in database Nov. 16, 1984; Accessed Aug. 20, 2013.*
U.S. Office Action dated Jun. 22, 2009, issued in corresponding U.S. Appl. No. 11/947,011.
U.S. Office Action dated Sep. 3, 2009, issued in corresponding U.S. Appl. No. 11/743,778.
U.S. Office Action dated Sep. 8, 2009, issued in corresponding U.S. Appl. No. 11/765,033.
U.S.Office Action dated Jun. 1, 2010, issued in corresponding U.S. Appl. No. 11/765,056.
U.S. Office Action dated Jan. 8, 2010, issued in corresponding U.S. Appl. No. 11/514,254.

(Continued)

Primary Examiner — Alicia L Otton
(74) Attorney, Agent, or Firm — Stein IP, LLC

(57) ABSTRACT

A benzoxazine-based monomer, a polymer thereof, an electrode for a fuel cell including the same, an electrolyte membrane for a fuel cell including the same, and a fuel cell using the same. The aromatic ring may contain up to 2 nitrogens within the ring. Single ring and fused ring substituents are attached to the pendent nitrogen. The ring substituents may be heterocyclic.

13 Claims, 10 Drawing Sheets

(56) References Cited

U.S. PATENT DOCUMENTS

| | | |
|---|---|---|
| 2008/0157422 A1 | 7/2008 | Lee et al. |
| 2009/0075147 A1 | 3/2009 | Kitamura et al. |
| 2009/0117436 A1 | 5/2009 | Choi et al. |
| 2009/0117440 A1 | 5/2009 | Choi et al. |
| 2010/0273087 A1 | 10/2010 | Choi et al. |
| 2011/0189581 A1 | 8/2011 | Choi et al. |

FOREIGN PATENT DOCUMENTS

| | | |
|---|---|---|
| DE | 603 02 673 | 8/2006 |
| EP | 1 247 844 | 10/2002 |
| EP | 1 253 661 | 10/2002 |
| EP | 1 760 110 | 3/2007 |
| EP | 1 881 549 | 1/2008 |
| JP | 10-25343 | 1/1998 |
| JP | 11-503262 | 3/1999 |
| JP | 11-97011 | 4/1999 |
| JP | 2001-19844 | 1/2001 |
| JP | 2001-270891 | 10/2001 |
| JP | 2001-271070 | 10/2001 |
| JP | 2002-260682 | 9/2002 |
| JP | 2003-12747 | 1/2003 |
| JP | 2003-12924 | 1/2003 |
| JP | 2003-286320 | 10/2003 |
| JP | 2003-327694 | 11/2003 |
| JP | 2004-43547 | 2/2004 |
| JP | 2004-103494 | 4/2004 |
| JP | 2004-149779 | 5/2004 |
| JP | 2004-179514 | 6/2004 |
| JP | 2005-41936 | 2/2005 |
| JP | 2005-82690 | 3/2005 |
| JP | 2005-283082 | 10/2005 |
| JP | 2006-339065 | 12/2006 |
| JP | 2007-70631 | 3/2007 |
| JP | 2007-214108 | 8/2007 |
| KR | 10-2006-0011831 | 2/2006 |
| KR | 10-2006-0055291 | 5/2006 |
| KR | 10-2007-0025626 | 3/2007 |
| KR | 10-2007-0025627 | 3/2007 |
| KR | 10-0745741 | 7/2007 |
| KR | 10-2007-0102579 | 10/2007 |
| WO | WO 96/13872 | 5/1996 |
| WO | WO 02/14334 | 2/2002 |
| WO | WO 02/057279 | 7/2002 |
| WO | WO 03/072638 | 9/2003 |
| WO | WO 2004/009708 | 1/2004 |
| WO | WO 2004/101509 | 11/2004 |
| WO | WO 2005/000955 | 1/2005 |
| WO | WO 2006/132207 | 12/2006 |

OTHER PUBLICATIONS

U.S. Office Action dated Jan. 15, 2010, issued in corresponding U.S. Appl. No. 11/947,011.
U.S. Office Action dated Feb. 19, 2010, issued in corresponding U.S. Appl. No. 11/743,778.
U.S. Office Action dated Mar. 30, 2010, issued in corresponding U.S. Appl. No. 11/947,011.
U.S. Office Action dated May 6, 2010, issued in corresponding U.S. Appl. No. 11/514,254.
U.S. Office Action dated Jun. 17, 2010, issued in corresponding U.S. Appl. No. 11/765,033.
U.S. Office Action dated Jul. 11, 2011, issued in corresponding U.S. Appl. No. 12/208,492.
U.S. Office Action dated Aug. 11, 2011, issued in corresponding U.S. Appl. No. 12/247,338.
U.S. Office Action dated Aug. 18, 2011, issued in corresponding U.S. Appl. No. 12/266,039.
U.S. Office Action dated Sep. 2, 2011, issued in corresponding U.S. Appl. No. 12/262,854.
U.S. Office Action dated Sep. 12, 2011, issued in corresponding U.S. Appl. No. 12/263,011.
U.S. Office Action dated Nov. 14, 2011, issued in corresponding U.S. Appl. No. 12/208,492.
U.S. Office Action dated Dec. 12, 2011, issued in corresponding U.S. Appl. No. 12/263,011.
U.S. Office Action dated Dec. 22, 2011, issued in corresponding U.S. Appl. No. 12/247,338.
U.S. Office Action dated Jan. 20, 2012, issued in corresponding U.S. Appl. No. 11/947,011.
U.S. Notice of Allowance dated Jan. 31, 2012, issued in corresponding U.S. Appl. No. 12/266,039.
U.S. Office Action dated Feb. 2, 2012, issued in corresponding U.S. Appl. No. 12/208,664.
U.S. Notice of Allowance dated Feb. 3, 2012, issued in corresponding U.S. Appl. No. 12/208,492.
U.S. Notice of Allowance dated Feb. 3, 2012, issued in corresponding U.S. Appl. No. 12/262,854.
U.S. Notice of Allowance dated Mar. 14, 2012, issued in corresponding U.S. Appl. No. 12/263,011.
U.S. Notice of Allowability dated Mar. 22, 2012, issued in corresponding U.S. Appl. No. 12/263,011.
U.S. Office Action dated Apr. 26, 2012, issued in corresponding U.S. Appl. No. 11/947,011.
U.S. Office Action dated May 10, 2012, issued in corresponding U.S. Appl. No. 12/247,338.
U.S. Notice of Allowance dated Jul. 11, 2012, issued in corresponding U.S. Appl. No. 12/247,338.
Seong-Woo Choi et al., "*Synthesis, characterization and thermal degradation of functional benzoxazine monomers and polymers containing phenylphosphine oxide*", Polymer Degradation and Stability 91 (2006), pp. 1166-1178.
Seong-Woo Choi, et al., Polybenzoxazine Based Membrane with Enhanced Oxygen Permeability Inducing Fluorine Containing Benzoxazine Monomer as an Electrode Additive and Binder for High Temperature PEM Fuel Cells; slides of presentation at 212$^{th}$ ECS, Washington, DC, Oct. 9, 2007.
STN Registry database entries for RN 35141-82-3, RN 35141-83-4 and RN 35141-84-5, Database entry date Nov. 16, 1984. Accessed Jan. 26, 2012.
Tarek AGAG, Journal of Applied Polymer Science, vol. 100, pp. 3769-3777 (2006).
212$^{th}$ ECS Meeting—Washington DC, Oct. 7-12, 2007, Program Information, B10—Proton Exchange Membrane Fuel Cells (PEMFC 7) Energy Technology/Physical and Analytical Electrochemistry/Battery/Industrial Electrochemistry and Electrochemical Engineering.
B. Antalek. "Using Pulsed Gradient Spin Echo NMR for Chemical Mixture Analysis: How to Obtain Optimum Results.", Concepts in Magnetic Resonance (2002) vol. 14(4), pp. 225-258.
S. Viel et al. "Diffusion-Ordered NMR Spectroscopy: A Versatile Tool for the Molecular Weight Determination of Uncharged Polysaccharides.", Biomacromolecules (2003) vol. 4, pp. 1843-1847.
D. A. Jayawickrama et al. "Polymer additives mixture analysis using pulsed-field gradient NMR spectroscopy.", Magn.Reson. Chem (1998), vol. 36, pp. 755-760.
K. Nishinari et al. "Soulution Properties of Pullulan.", Macromolecules (1991) vol. 24, pp. 5590-5593.
L.C. Van Gorkom et al. "Analysis of DOSY and GPC-NMR Experiments on Polymers by Multivariate Curve Resolution.", Journal of Magnetic Resonance (1998) vol. 130, pp. 125-130.
A. Chen et al. "Determination of Molecular Weight Distributions for Polymers by Diffusion-Ordered NMR.", J. Am. Chem. Soc. (1995) vol. 117, pp. 7965-7970.
Hajime Kimura et al. "Epoxy Resin Cured by Bisphenol a Based Benzoxazine.", Journal of Applied Polymer Science (1998), vol. 68, pp. 1903-1910.
Schuster, Martin F.H., et al., "Anhydrous Proton-Conducting Polymers", Annu. Rev. Mater. Res., vol. 33, 2003, pp. 233-261.
Yamada, M. et al., "Anhydrous proton conducting polymer electrolytes based on poly(vinylphosphonic acid)-heterocyclic composite material", Polymer, vol. 46, No. 9, 2005, pp. 2986-2992.
Pu, H., et al., "Proton Transport in Polybenzimidazole Blended with $H_3PO_4$ or $H_2SO_4$", J. Polymer Science, Part B: Polymer Physics, vol. 40, 2002, pp. 663-669.

(56) References Cited

OTHER PUBLICATIONS

Kim, Hyoung-Juhn et al. *Polybenzimidazoles for High Temperature Fuel Cell Application*. Macromol. Rapid Commun. 2004, vol. 25, pp. 1410-1413.
Ueda, Mitsuru et al. *Poly(benzimidazole) Synthesis by Direct Reaction of Methoxyphthalic Acids and Tetramine.* J. Poly. Sci. Part A: Polym. Chem, 27 pp. 2815-2818 (1989).
Choi et al., "Synthesis, characterization and thermal degradation of functional benzoxazine monomers and polymers containing phenylphosphine oxide", Polymer Degradation and Stability, vol. 91, No. 5, May 1, 2006, pp. 1166-1178.
Low, Hong Yee, et al. "Structural Effects of Phenols on the Thermal and Thermo-oxidative Degradation of Polybenzoxazines". Polymer, vol. 40, No. 15. Jul. 1999. pp. 4365-4376.
Kim, H.J., et al. "Synthesis and Thermal Characterization of Polybenzoxazines Based on Acetylene-functional Monomers". Polymer, vol. 40, No. 23. Nov. 1999. pp. 6565-6573.
Shen, Shyan Bob, et al. "Synthesis and Characterization of Polyfunctional Naphthoxazines and Related Polymers". Journal of Applied Polymer Science vol. 61, No. 9. 1996, pp. 1595-1605.
Lin et al., "Synthesis and Properties of Flame-Retardant Benzoxazines by Three Approaches", Journal of Polymer Science, Part A: Polymer Chemistry, vol. 44, 2006, pp. 3454-3468.
Hirai et al., "Air-Induced *anti*-Markovnikov Addition of Secondary Phosphine Oxides and H-Phosphinates to Alkenes", National Institute of Advanced Industrial Science and Technology, Organic Letters 2007, vol. 9, No. 1, pp. 53-55.
Beletskaya et al., "Arylation of 6$H$-Dibenzo[c,e][1,2 $\lambda^5$]oxaphosphinine 6-Oxide", Russian Journal of Organic Chemistry, vol. 40, No. 12, 2004, pp. 1782-1786.
Yamada et al., "A Novel Synthesis of 6-Hydroxyalkyl- and 6-Hydroxy-aralkyl-6$H$dibenz[c,e][1,2]oxaphosphorin 6-Oxides", vol. 27, 1990, pp. 845-850.
Human translation of JP 2003-286320, A. Takeichi et al., Oct. 2003.
Human translation of JP 2004-103494, Kimura et al., Apr. 2004.
Machine translation of JP 2004-149779, Sakaguchi et al., May 2004.
European Search Report issued in European Patent Application No. 06254551.2-2115 on Nov. 21, 2006.
European Office Action issued in corresponding European Patent Application No. 07250814.6 on Oct. 30, 2007.
European Search Report issued in European Patent Application No. 08104319.2 on Oct. 13, 2008.
European Search Report issued in European Patent Application No. 08157494.9 on Nov. 24, 2008.
European Office Action dated Dec. 4, 2008, issued in corresponding European Patent Application No. 08164095.5.
European Search Report issued in European Patent Application No. 08164096.3 on Jan. 20, 2009.
European Search Report issued in European Patent Application No. 08166328.8 on Jan. 22, 2009.
European Search Report issued in European Patent Application No. 08168081.1 on Jan. 28, 2009.
Extended European Search Report issued in European Patent Application No. 08168032.4 on Feb. 3, 2009.
European Search Report issued in European Patent Application No. 08168404.5 on Feb. 10, 2009.
Extended European Search Report issued in European Patent Application No. 08168404.5 on Apr. 23, 2009.
European Search Report dated Jul. 21, 2010 issued in corresponding European Patent Application No. 10164784.0.
European Search Report dated Jul. 21, 2010 issued in corresponding European Patent Application No. 10164785.7.
Japanese Office Action issued in Japanese Patent Application No. 2006-239572 on Feb. 17, 2009.
Japanese Office Action dated Jun. 21, 2011, issued in corresponding Japanese Patent Application No. 2007-309320.
Japanese Office Action dated Sep. 20, 2011, issued in corresponding Japanese Patent Application No. 2008-233675.
Japanese Office Action dated Oct. 23, 2011, issued in corresponding Japanese Patent Application No. 2007-309320.
Korean Office Action dated Jul. 21, 2010, issued in corresponding Korean Patent Application No. 10-2008-0089999.
Korean Office Action dated Oct. 6, 2010, issued in corresponding Korean Patent Application No. 10-2008-0099549.
U.S. Appl. No. 11/514,254, filed Sep. 1, 2006, Seong-woo Choi et al., Samsung SDI Co., Ltd.
U.S. Appl. No. 11/514,831, filed Sep. 5, 2006, Seong-woo Choi et al., Samsung SDI Co., Ltd.
U.S. Appl. No. 11/743,778, filed May 3, 2007, Seong-woo Choi et al., Samsung SDI Co., Ltd.
U.S. Appl. No. 11/856,350, filed Sep. 17, 2007, Seong-woo Choi et al., Samsung SDI Co., Ltd.
U.S. Appl. No. 11/947,011, filed Nov. 29, 2007, Seong-woo Choi et al., Samsung Electronics Co., Ltd.
U.S. Appl. No. 12/208,492, filed Sep. 11, 2008, Seong-woo Choi et al., Samsung Electronics Co., Ltd.
U.S. Appl. No. 12/208,664, filed Sep. 11, 2008, Seong-woo Choi et al., Samsung Electronics Co., Ltd.
U.S. Appl. No. 11/765,033, filed Jun. 19, 2007, Hee-young Sun et al., Samsung SDI Co., Ltd.
U.S. Appl. No. 11/765,065, filed Jun. 19, 2007, Kyung-jung Kwon et al., Samsung SDI Co., Ltd.
U.S. Appl. No. 12/247,338, filed Oct. 8, 2008, Seong-woo Choi et al., Samsung Electronics Co., Ltd.
U.S. Appl. No. 12/263,011, filed Oct. 31, 2008, Seong-woo Choi et al., Samsung Electronics Co., Ltd.
U.S. Appl. No. 12/262,854, filed Oct. 31, 2008, Seong-woo Choi et al., Samsung Electronics Co., Ltd.
U.S. Appl. No. 12/266,039, filed Nov. 6, 2008, Seong-woo Choi et al., Samsung Electronics Co., Ltd.
U.S. Appl. No. 13/464,517, filed May 4, 2012, Seong-woo Choi et al., Samsung Electronics Co., Ltd.
U.S. Appl. No. 13/466,750, filed May 8, 2012, Seong-woo Choi et al., Samsung Electronics Co., Ltd.
U.S. Appl. No. 13/466,843, filed May 8, 2012, Seong-woo Choi et al., Samsung Electronics Co., Ltd.
U.S. Appl. No. 13/478,893, filed May 23, 2012, Seong-woo Choi et al., Samsung Electronics Co., Ltd.
U.S. Appl. No. 13/523,516, filed Jun. 14, 2012, Seong-woo Choi et al., Samsung Electronics Co., Ltd.

\* cited by examiner

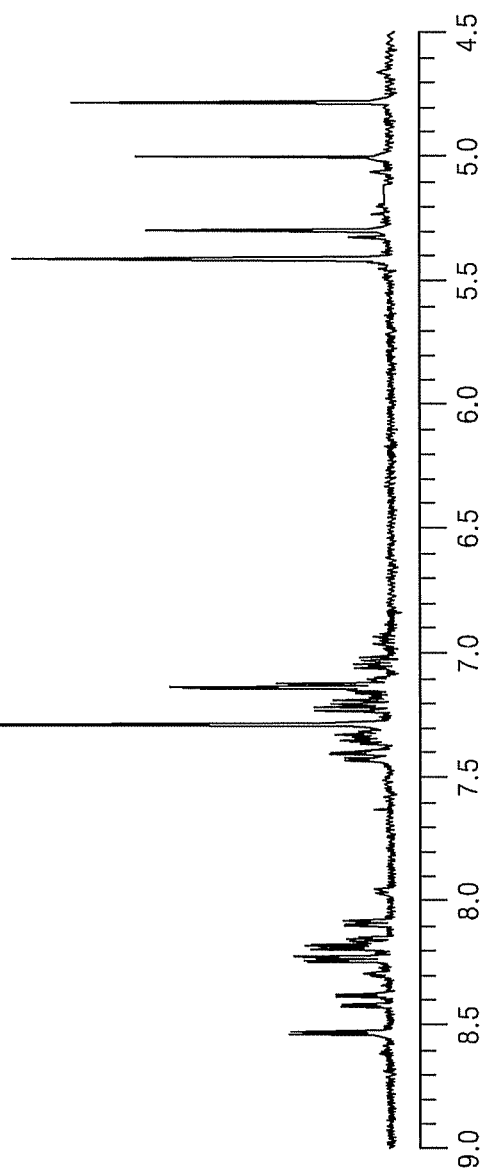

BENZOXAZINE-BASED MONOMER, POLYMER THEREOF, ELECTRODE FOR FUEL CELL INCLUDING THE SAME, ELECTROLYTE MEMBRANE FOR FUEL CELL INCLUDING THE SAME, AND FUEL CELL USING THE SAME

CROSS-REFERENCE TO RELATED PATENT APPLICATION

This is a divisional application of U.S. patent application Ser. No. 12/208,664, filed Sep. 11, 2008, now U.S. Pat. No. 8,252,890, issued Aug. 28, 2012, which claims the benefit of Korean Patent Application No. 10-2007-0092146, filed on Sep. 11, 2007 in the Korean Intellectual Property Office, the disclosures of which are incorporated herein in their entirety by reference.

BACKGROUND OF THE INVENTION

1. Field of the Invention

Aspects of the present invention relate to a benzoxazine-based monomer, a polymer thereof, an electrode for a fuel cell including the same, an electrolyte membrane for a fuel cell including the same, and a fuel cell using the same. For purposes of this application, "benzoxazine-based monomer" shall mean that the aromatic ring may contain up to 2 nitrogens within the ring. Single ring and fused ring substituents are attached to the pendent nitrogen. The ring substituents may be heterocyclic.

2. Description of the Related Art

Fuel cells using a polymer electrolyte membrane as an electrolyte, which operate at a relatively low temperature and can be miniaturized, are regarded as an alternative power source for automobiles and for residential distributed power generation systems. A known polymer electrolyte membrane used in polymer electrolyte membrane fuel cells are the perfluorosulfonic acid polymers represented by NAFION® (DuPont Company).

However, these polymer electrolyte membranes must be hydrated to retain proton conductivity. In addition, the fuel cell system needs to be operated at 100° C. or higher in order to improve the system efficiency. However, the electrolyte membrane cannot function as a solid electrolyte at such a high temperature since moisture evaporates from the electrolyte membrane.

A non-hydrated electrolyte membrane that can be operated at 100° C. or higher has been developed in order to overcome these problems. For example, polybenzimidazole doped with phosphoric acid as a material used to form a non-hydrated electrolyte membrane is disclosed in U.S. Pat. No. 5,525,436.

In addition, in fuel cells using a perfluorosulfonic acid polymer membrane that operates at a low-temperature, a hydrophobic electrode obtained by mixing the perfluorosulfonic acid polymer with water-repellent polytetrafluoroethylene (PTFE) is used in order to improve gas diffusion that is otherwise blocked by water generated in a cathode (Japanese Patent Laid-Open Publication No. hei 05-283082).

Meanwhile, in fuel cells using polybenzimidazole (PBI) doped with phosphoric acid, which is a high-temperature non-hydrated electrolyte for an electrolyte membrane, attempts to impregnate an electrode with liquid state phosphoric acid have been made and attempts to increase the loading amount of a metal catalyst have been made in order to facilitate interface contact between the electrode and the membrane. These attempts, however, do not sufficiently improve characteristics of the fuel cells.

When air is supplied to a cathode in a solid polymer electrolyte membrane doped with phosphoric acid, activation takes about a week even if the electrode composition is optimized. Although a fuel cell can have improved efficiency and activation time can be decreased by replacing air with oxygen, the use of oxygen is not preferred for commercialization.

SUMMARY OF THE INVENTION

Aspects of the present invention provide a benzoxazine-based monomer having improved wettability of phosphoric acid in an electrode, high thermal resistance, high phosphoric acid resistance and excellent affinity for an acid; a polymer of the benzoxazine-based monomer; an electrode for a fuel cell including the same; an electrolyte membrane for a fuel cell including the same; and a fuel cell using the same.

An embodiment of the present invention provides a benzoxazine-based monomer represented by Formula 1 below.

Formula 1

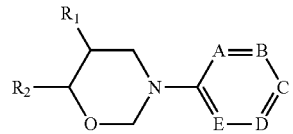

Here, A, B, C, D and E are carbon, or one or two of A, B, C, D and E are nitrogen and the others are carbon, and $R_1$ and $R_2$ are connected to each other to form a ring, wherein the ring is a C6-C10 cycloalkyl group, a C3-C10 heteroaryl group, a fused C3-C10 heteroaryl group, a C3-C10 heterocyclic group or a fused C3-C10 heterocyclic group.

Another embodiment of the present invention provides a polymer of a benzoxazine-based monomer that is a polymerization product of the benzoxazine-based monomer or a polymerization product of the benzoxazine-based monomer and a crosslinkable compound.

Another embodiment of the present invention provides an electrode for a fuel cell including the polymer of a benzoxazine-based monomer and a catalyst. Another embodiment of the present invention provides an electrolyte membrane for a fuel cell including a polymer of a polybenzoxazine-based compound that is a polymerization product of the benzoxazine-based monomer and a crosslinkable compound. Another embodiment of the present invention provides a fuel cell including the electrode. Another embodiment of the present invention provides a fuel cell including the electrolyte membrane.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 2B is an expanded portion of FIG. 2A;

DETAILED DESCRIPTION OF THE EMBODIMENTS

Figure 1:
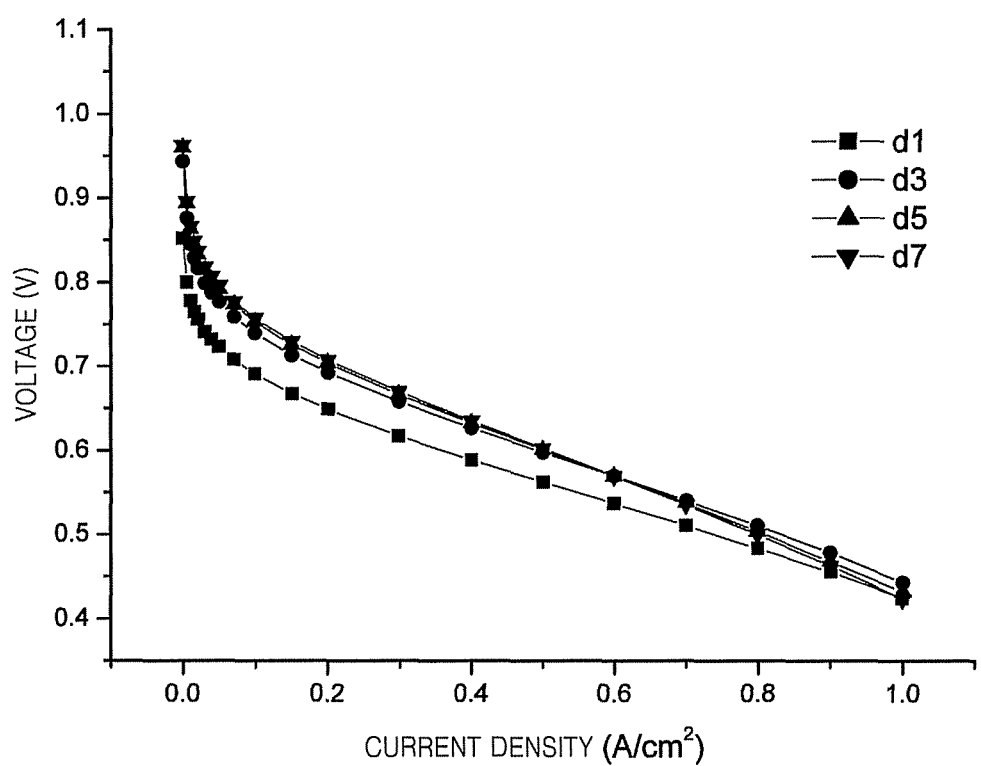
FIG. 1 is a graph illustrating the current density-voltage characteristics of a fuel cell prepared according to Example 1.

Reference will now be made in detail to the present embodiments of the present invention, examples of which are illustrated in the accompanying drawings. The embodiments are described below in order to explain the present invention by referring to the figures.

An embodiment of the present invention provides a benzoxazine-based monomer represented by Formula 1.

Formula 1

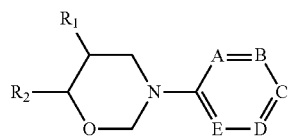

Here, A, B, C, D and E are carbon, or one or two of A, B, C, D and E are nitrogen and the others are carbon, $R_1$ and $R_2$ are connected to each other to form a ring, and the ring is a C6-C10 cycloalkyl group, a C3-C10 heteroaryl group, a fused C3-C10 heteroaryl group, a C3-C10 heterocyclic group or a fused C3-C10 heterocyclic group.

The ring formed by $R_1$ and $R_2$ in Formula 1 may be represented by the formulae below.

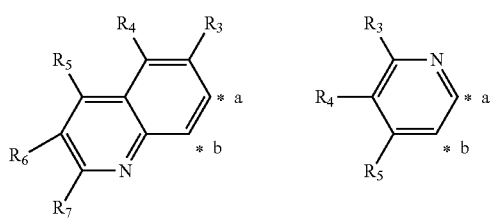

-continued

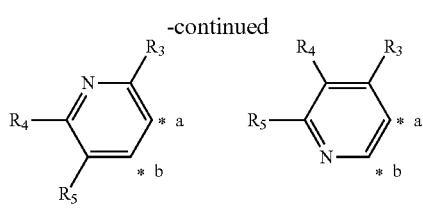

Here, $R_3$ to $R_7$ are each independently a hydrogen atom, a C1-C10 alkyl group, a C6-C10 aryl group, a halogen atom, a cyano group, a hydroxyl group, a C6-C10 cycloalkyl group, a C1-C10 heteroaryl group or a C1-C10 heterocyclic group, wherein *a is bonded to Formula 1 at $R_1$ 1 and *b is bonded to Formula 1 at $R_2$.

The

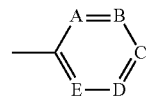

of Formula 1 is represented by the formulae below.

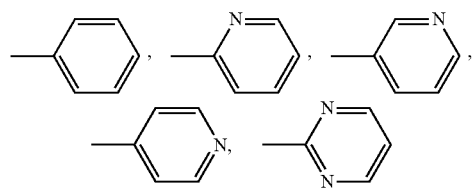

The benzoxazine-based monomer according to an embodiment of the present invention has a structure capable of improving affinity for an acid. According to an embodiment of the present invention, when the benzoxazine-based monomer represented by Formula 10, below, is added to an electrode for a fuel cell, the benzoxazine-based monomer of Formula 10 is transformed to a structure having a plurality of quaternary amines through ring opening polymerization while the fuel cell is operating and thus traps an acid as shown in Reaction Scheme 1.

Reaction Scheme 1

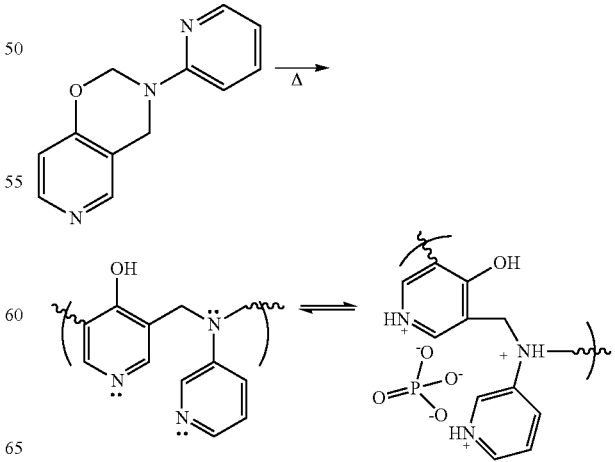

Due to the acid-trapping function of the benzoxazine-based monomer, the benzoxazine-based monomer in an electrode for a fuel cell improves wettability of phosphoric acid ($H_3PO_4$) to the electrode, thermal resistance and phosphoric acid resistance. In addition, since phosphoric acid is retained in micropores of the electrode, flooding caused by phosphoric acid infiltrating into macropores of the electrode, which inhibits gas diffusion because of the large amount of liquid state phosphoric acid in the electrode, can be effectively prevented. Accordingly, comparability can be increased in the interfaces among the gaseous state (fuel gas or oxidizing gas)—the liquid state (phosphoric acid)—and the solid state (catalyst). In addition, the benzoxazine-based monomer is self polymerized by heat generated at an operating temperature to form a thermosetting polymer, which improves the stability of interfaces of the electrode.

The benzoxazine-based monomer may be one of the compounds represented by Formulae 1A to 1D.

Formula 1A

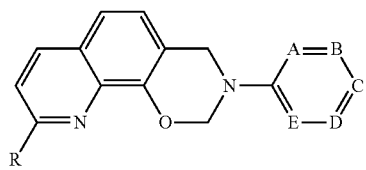

Here, R is a hydrogen atom or a C1-C10 alkyl group.

Formula 1B

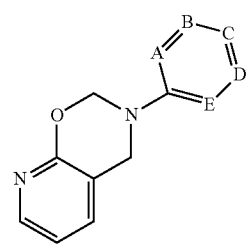

Formula 1C

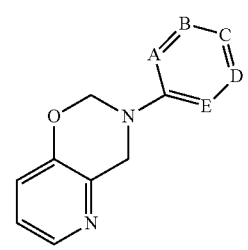

Formula 1D

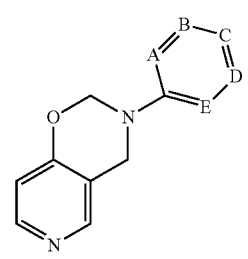

Here, the

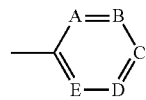

of Formulae 1A to 1D is represented by the formulae below.

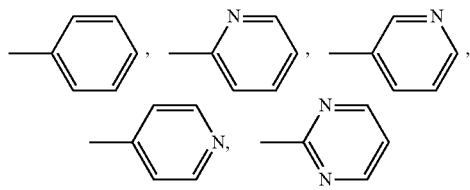

The benzoxazine-based monomer represented by Formula 1 can be synthesized using a phenol compound having a pyridine or pyridine derivative as a starting material, an amine compound and p-formaldehyde. The conditions for the reaction are not limited. For example, the reaction can be performed by a melt process without a solvent at a temperature in the range of 80 to 100° C., and the temperature may vary according to the types of substituents.

Hereinafter, a method of preparing the benzoxazine-based monomer represented by Formula 1 according to aspects of the present invention will be described. For example, compounds represented by Formulae 1A and 1B are described, but other compounds can be synthesized in a similar manner.

First, as shown in Reaction Scheme 2, below, the benzoxazine-based monomers represented by Formulae 1A and Formula 1B can be prepared by heating a mixture of 8-hydroxyquinoline (A), p-formaldehyde (B) and an amine compound (C) without a solvent, or can be prepared by adding a solvent to the mixture, refluxing the mixture, and performing a work-up process of the resultant.

Reaction Scheme 2

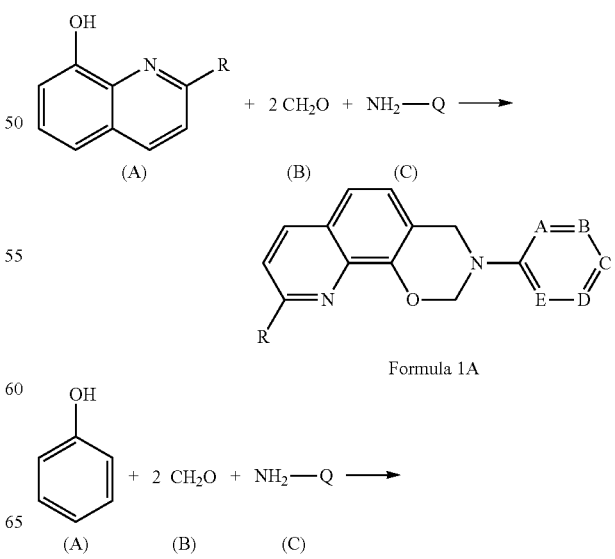

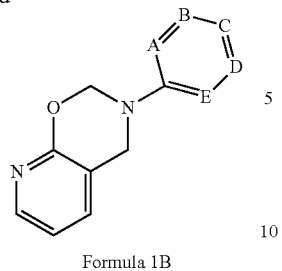

Formula 1B

Here, R is a hydrogen atom or a C1-C10 alkyl group, and -Q is

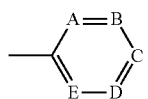

which is one of the formulae below.

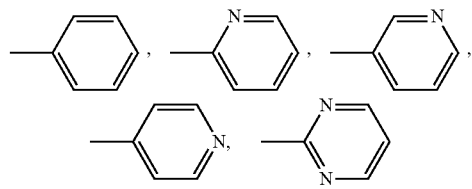

When a solvent is used, 1,4-dioxane, chloroform, dichloromethane, tetrahydrofuran (THF), or the like can be used as the solvent. The heating temperature may be in the range of 50 to 90° C. and preferably about 80° C., and can be adjusted to a temperature at which the solvent can be refluxed.

The benzoxazine-based monomer represented by Formula 1 according to an embodiment of the present invention may be compounds represented by Formulae 2 to 21.

Formula 2

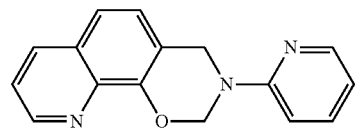

Formula 3

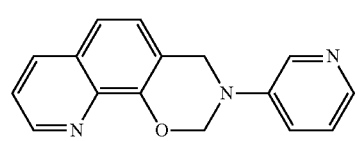

Formula 4

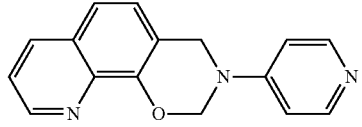

Formula 5

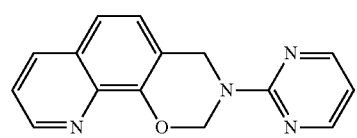

Formula 6

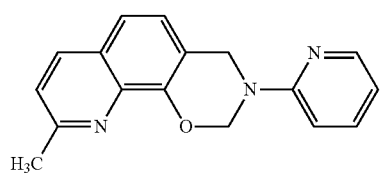

Formula 7

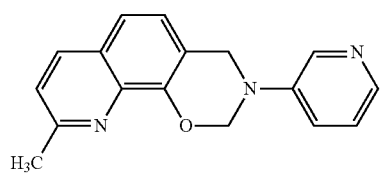

Formula 8

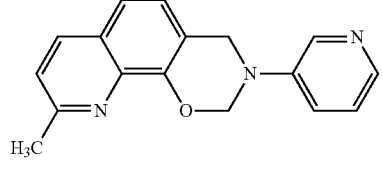

Formula 9

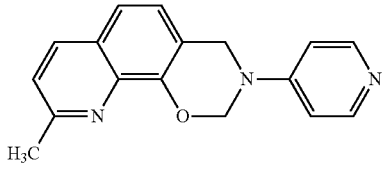

Formula 10

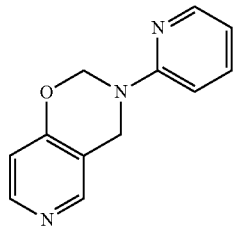

Formula 11

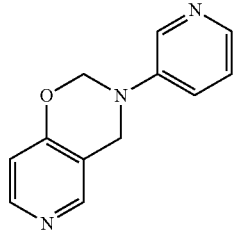

Formula 12

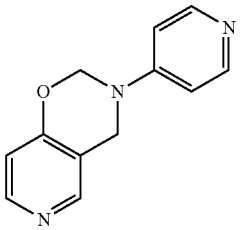

Formula 13
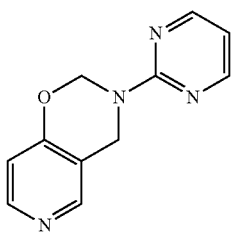

Formula 14
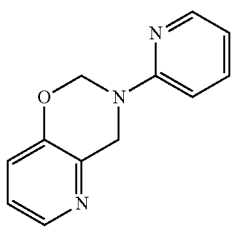

Formula 15
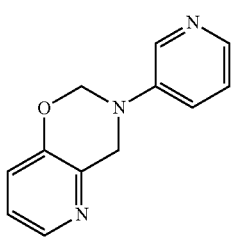

Formula 16
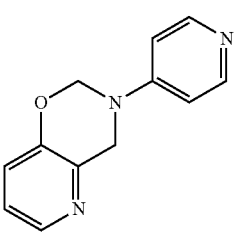

Formula 17
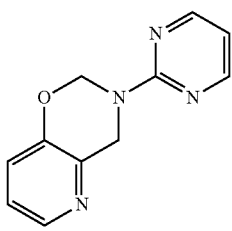

Formula 18
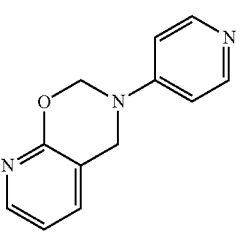

Formula 19
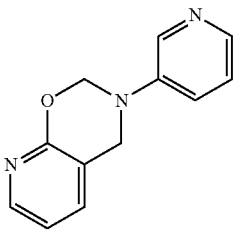

Formula 20
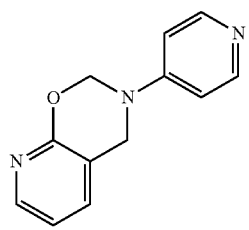

Formula 21
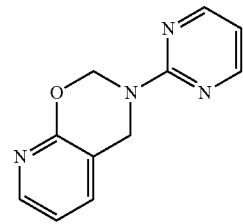

A benzoxazine-based monomer according to an embodiment of the present invention has good affinity for acids generally, a high phosphoric acid resistance and high thermal resistance. When used in the preparation of an electrode and an electrolyte membrane for a fuel cell, the benzoxazine-based monomer can have a tertiary amine structure in which the backbone of the main chain has an affinity for phosphoric acid through ring-opening polymerization. In other words, the affinity for phosphoric acid is increased to maximize the capacity of phosphoric acid. Thus, wettability of phosphoric acid ($H_3PO_4$) at the three phase interface of the electrode can be improved and the amount of phosphoric acid flowing into the electrode can be increased. Particularly, oxygen permeation can be improved, and wettability of phosphoric acid ($H_3PO_4$) and thermal stability can be improved in the electrode even when air is used in a cathode. Therefore, the fuel cells employing the electrode and the electrolyte membrane including the benzoxazine-based monomer can have excellent utility, high conductivity, and long lifetime, and can operate at a high temperature with no humidity, and can have excellent power generation efficiency.

Examples of the C1-C20 alkyl group are a methyl group, an ethyl group, a propyl group, an isobutyl group, a sec-butyl group, a pentyl group, an iso-amyl group, and a hexyl group, and at least one of the hydrogen atoms can be substituted with a halogen atom, a C1-C20 alkyl group substituted with a halogen atom (e.g.: $CCF_3$, $CHCF_2$, $CH_2F$ and $CCl_3$), a hydroxyl group, a nitro group, a cyano group, an amino group, an amidino group, a hydrazine, a hydrazone, a carboxyl group or a salt thereof, a sulfonic acid group or a salt thereof, a phosphoric acid or a salt thereof, a saturated C1-C20 alkyl group, a C2-C20 alkenyl group, a C2-C20 alkynyl group, a C1-C20 heteroalkyl group, a C6-C20 aryl group, a C6-C20 arylalkyl group, a C6-C20 heteroaryl group or a C6-C20 heteroarylalkyl group.

The aryl group as used herein is used alone or in a combination, and is a carbocyclic aromatic system having 6 to 20 carbon atoms and one or more rings. The rings can be attached to each other or fused with each other using a pendent method. The term "aryl" includes an aromatic radical such as phenyl, naphthyl, and tetrahydronapththyl. The aryl group may include a substituent of a haloalkylene group, a nitro group, a cyano group, an alkoxy group, and a short chain alkylamino group. In addition, at least one of the hydrogen atoms can be substituted with the same functional groups described above for the C1-C20 alkyl group.

The heteroaryl group as used herein indicates a monovalent monocyclic or bivalent bicyclic aromatic organic compound including C1-C20 carbon rings and including 1, 2, or 3 hetero atoms selected from the group consisting of nitrogen, oxygen, phosphorus and sulfur. Examples of the heteroaryl group are pyrazinyl, furanyl, thienyl, pyridyl, pyrimidinyl, isothiazolyl, oxazolyl, thiazolyl, triazolyl and 1,2,4-thiadiazolyl.

The fused heteroaryl group as used herein indicates a single-ring or double-ring system composed of about 8 to 11 rings in which at least one atom is an atom other than a carbon atom, such as nitrogen, oxygen or sulfur.

At least one of the hydrogen atoms of the heteroaryl group and the fused heteroaryl group can be substituted with the same functional groups described above for the C1-C20 alkyl group.

The heterocyclic group as used herein indicates five-ten-membered ring including hetero atoms such as nitrogen, sulfur, phosphor and oxygen. At least one of the hydrogen atoms of the heterocyclic group can be substituted with the same functional groups described above for the C1-C20 alkyl group. The fused heterocyclic group as used herein is a single-ring or double-ring system of the heterocyclic group.

The C6-C10 cycloalkyl group as used herein indicates a carbocycle having 6 to 10 carbon atoms, and at least one of hydrogen atoms can be substituted with the same functional groups described above for the C1-C20 alkyl group.

Aspects of the present invention also provide a polymer of the benzoxazine-based monomer that is a polymerization product of the benzoxazine-based monomer represented by Formula 1. The polymer can be prepared by dissolving the benzoxazine-based monomer in a solvent and polymerizing the solution through heat-treatment. The heat-treatment may be performed at a temperature in the range of 150 to 240° C. When the heat-treatment temperature is less than 150° C., the extent of the polymerization reaction may be decreased. On the other hand, when the temperature is higher than 240° C., other compounds or polymers generated from side reactions may decrease yields of the desired products. A polymerization catalyst can be used, if required. The solvent may be N-methylpyrrolidone (NMP), dimethylacetamide (DMAc), or the like, and the amount of the solvent may be in the range of 5 to 95 parts by weight based on 100 parts by weight of benzoxazine-based monomer.

An embodiment of the present invention also provides a polymer of a benzoxazine-based monomer that is a polymerization product of the benzoxazine-based monomer represented by Formula 1 and a crosslinkable compound. The crosslinkable compound may be at least one of polybenzimidazole (P81), a polybenzimidazole-base complex, polybenzthiazole, polybenzoxazole and polyimide, but is not limited thereto. The amount of the crosslinkable compound may be in the range of 5 to 95 parts by weight based on 100 parts by weight of the benzoxazine-based monomer represented by Formula 1.

An electrode for a fuel cell according to an embodiment of the present invention includes a catalyst layer incorporating a polymer that is a polymerization product of the benzoxazine-based monomer represented by Formula 1 or a polymerization product of the benzoxazine-based monomer represented by Formula 1 and the crosslinkable compound. The catalyst layer includes a catalyst.

The polymer of the benzoxazine-based monomer represented by Formula 1 is also used as a binder for the electrode, and thus a conventional binder is not necessary. The polymer of the benzoxazine-based monomer represented by Formula 1 improves the wettability of phosphoric acid. The amount of the polymer may be in the range of 0.1 to 65 parts by weight based on 100 parts by weight of the catalyst. When the amount of the polymer is less than 0.1 parts by weight, the wet state of the electrode is not sufficiently improved. On the other hand, when the amount of the polymer is greater than 65 parts by weight, flooding may be increased.

The catalyst may be Pt, a metal-Pt alloy including Pt and at least one metal selected from the group consisting of Au, Pd, Rh, Ir, Ru, Sn, Mo, Co, and Cr, or a mixture including Pt and at least one metal selected from the group consisting of Au, Pd, Rh, Ir, Ru, Sn, Mo, Co, and Cr. Alternatively, the catalyst may be a support catalyst in which the catalyst metal is loaded on a carbonaceous support. In particular, the catalyst may be a catalyst metal including at least one of Pt, PtCo, and PtRu, or a support catalyst in which the catalyst metal is loaded on a carbonaceous support.

The electrode according to an embodiment of the present invention may further include a binder that is commonly used in the preparation of an electrode for fuel cells. The binder may be at least one of poly(vinylidenefluoride), polytetrafluoroethylene, a tetrafluoroethylene-hexafluoroethylene copolymer, and perfluoroethylene, and for improving wettability of the electrode the amount of the binder may be in the range of 0.1 to 50 parts by weight based on 100 parts by weight of the catalyst.

The crosslinkable compound may be at least one of polybenzimidazole (PBI), a polybenzimidazole-base complex, polybenzthiazole; polybenzoxazole and polyimide, but is not limited thereto. The amount of the crosslinkable compound may be in the range of 5 to 95 parts by weight based on 100 parts by weight of the benzoxazine-based monomer represented by Formula 1.

A method of preparing the electrode for a fuel cell will be described. First, a catalyst is dispersed in a solvent to prepare a dispersion. The solvent may be N-methylpyrrolidone (NMP), DMAc, or the like, and the amount of the solvent may be in the range of 100 to 1000 parts by weight based on 100 parts by weight of the catalyst. A mixture of a benzoxazine-based monomer represented by Formula 1, a solvent and a binder is added to the dispersion and mixed while stirring. The mixture may further include a crosslinkable compound. The solvent may be N-methylpyrrolidone (NMP), dimethyl acetamide (DMAc), or the like.

An electrode is prepared by coating the mixture on the surface of a carbon support. Here, the carbon support may be fixed on a glass substrate in order to facilitate coating. The coating can be performed using a doctor blade, a bar coating, screen printing, or the like, but the coating method is not limited thereto.

The coated mixture is dried at a temperature in the range of 20 to 150° C. to remove the solvent. The drying may be performed for 10 to 60 minutes, and the drying time may vary according to the drying temperature.

As described above, the electrode for a fuel cell does not include the benzoxazine-based monomer represented by Formula 1 but a polymer thereof since the benzoxazine-based monomer represented by Formula 1 is polymerized to form the polymer while the electrode is activated and/or while the fuel cell is operated. If a crosslinking agent is further added to the mixture of the benzoxazine-based monomer, the solvent, and the binder, the prepared electrode includes a polymer of the benzoxazine-based monomer and the crosslinkable compound.

Hereinafter, an electrolyte membrane and a method of preparing the electrolyte membrane according to an embodiment of the present invention will be described. An electrolyte membrane formed using a crosslinkable compound is described herein. However, when an electrolyte membrane is prepared only using the benzoxazine-based monomer represented by Formula 1, the preparation process is the same as that described herein, except that the crosslinkable compound is not used.

First, a phosphorus-containing benzoxazine-based monomer represented by Formula 1 is blended with a crosslinkable compound, and the mixture is cured at a temperature in the range of 50 to 250° C., and preferably 80 to 220° C. The cured mixture is impregnated with a proton conductor such as an acid to prepare an electrolyte membrane.

The crosslinkable compound may be at least one compound selected from the group consisting of polybenzimidazole (PBI), a polybenzimidazole-base complex, polybenzthiazole, polybenzoxazole, and polyimide. The polybenzimidazole-base complex is disclosed in Korean Patent Application No. 2007-102579 filed by the inventors of the present invention.

The amount of the crosslinkable compound may be in the range of 5 to 95 parts by weight based on 100 parts by weight of the benzoxazine-based monomer of Formula 1.

When the amount of the crosslinkable compound is less than 5 parts by weight, the proton conductivity may be decreased since phosphoric acid cannot be impregnated into the membrane. On the other hand, when the amount of the crosslinkable compound is greater than 95 parts by weight, gas may permeate since the crosslinked polybenzoxazines melt in polyphosphoric acid in the presence of an excessive amount of phosphoric acid.

Second, an electrolyte membrane is formed using a mixture of the first benzoxazine-based monomer represented by Formula 1 and the crosslinkable compound. The membrane may be formed using tape casting, or a conventionally used coating method. The coating method may be a method of casting the mixture on a support using a doctor blade. In this regard, the doctor blade having a 250-500 µm gap may be used.

In the formation of the membrane using the doctor blade method, a process of removing the support by exfoliating the electrolyte membrane from the support may further be included after the curing and before the impregnation with the proton conductor. In order to remove the support, the membrane may be immersed in distilled water at a temperature in the range of 60 to 80° C.

The support may be any material that can support the electrolyte membrane, for example, a glass substrate, polyimide film, and the like. Removal of the support by immersion is not necessary in the tape casting method, since the tape cast membrane is stripped from a support such as polyethylene terephthalate and placed in an oven for curing. In addition, when the membrane is formed using a mixture of benzoxazine-based monomer and polybenzimidazole through a tape casting method, filtering the mixture may further be included in the method.

The prepared membrane is cured through heat treatment, and impregnated with a proton conductor such as an acid to form an electrolyte membrane. The proton conductor may be phosphoric acid, a C1-C20 organic phosphonic acid, or the like, but is not limited thereto. The C1-C20 organic phosphonic acid may be methyl phosphonic acid, ethyl phosphonic acid, etc. The amount of the proton conductor may be 300 to 1000 parts by weight based on 100 parts by weight of the electrolyte membrane. For example, 85% by weight of an aqueous phosphoric acid solution may be used at 80° C. for 2.5 to 14 hours, but the concentration of the acid used in this embodiment of the present invention is not limited.

A method of preparing a fuel cell using the electrode according to an embodiment of the present invention will be described. Any electrolyte membrane that is commonly used in the preparation of fuel cells can be used herein. Alternatively, an electrolyte membrane including a crosslinked product of polybenzoxazine-based compounds that is prepared by polymerization of the benzoxazine-based monomer represented by Formula 1 and a crosslinkable compound can be used as well.

Performance of the fuel cell may be maximized by using an electrolyte membrane including the crosslinked product of polybenzoxazine-based compounds. For example, the electrolyte membrane may be a polybenzimidazole electrolyte membrane, a polybenzoxazine-polybenzimidazole copolymer electrolyte membrane, a PTFE porous membrane, or the like.

A process of preparing a membrane and electrode assembly for fuel cells according to an embodiment of the present invention will be described. Here, the "membrane and electrode assembly (MEA)" refers to a structure in which electrodes composed of a catalyst layer and a diffusion layer are laminated on both sides of an electrolyte membrane.

The MEA according to this embodiment the present invention may be prepared by placing electrodes including the catalyst layer on both sides of the obtained electrolyte membrane and combining them at a high temperature under a high pressure, and then further combining them with a fuel diffusion layer. The combining may be performed at a temperature at which the electrolyte membrane softens, that is, under 0.1 to 3 ton/cm$^2$, and preferably under about 1 ton/cm$^2$.

Then, a bipolar plate is installed into each membrane-electrode assembly to complete a fuel cell. The bipolar plate has a fuel supply groove and current collecting property. The fuel cell may be used as a polymer electrolyte membrane fuel cell (PEMFC), but is not limited thereto.

Hereinafter, aspects of the present invention will be described in greater detail with reference to the following examples. The following examples are for illustrative purposes only and are not intended to limit the scope of the invention.

Synthesis Example 1

Preparation of 3HP-3AP, represented by Formula 15

5 g (0.053 mol) of 3-hydroxypyridine, 3.67 g (0.116 mol) of p-formaldehyde and 5.46 g (0.058 mol) of 3-aminopyridine were added to a 100 ml one-neck round-bottom flask and mixed while held in an oil bath at 90° C. After about 30 minutes, when the initially opaque mixture became a yellow transparent gel type material, the reaction was quenched using chloroform, and then the mixture was cooled to room temperature. The cooled crude product was base-washed twice through solvent extraction using a 1N NaOH aqueous solution, and washed once with deionized water.

Figure 2A:
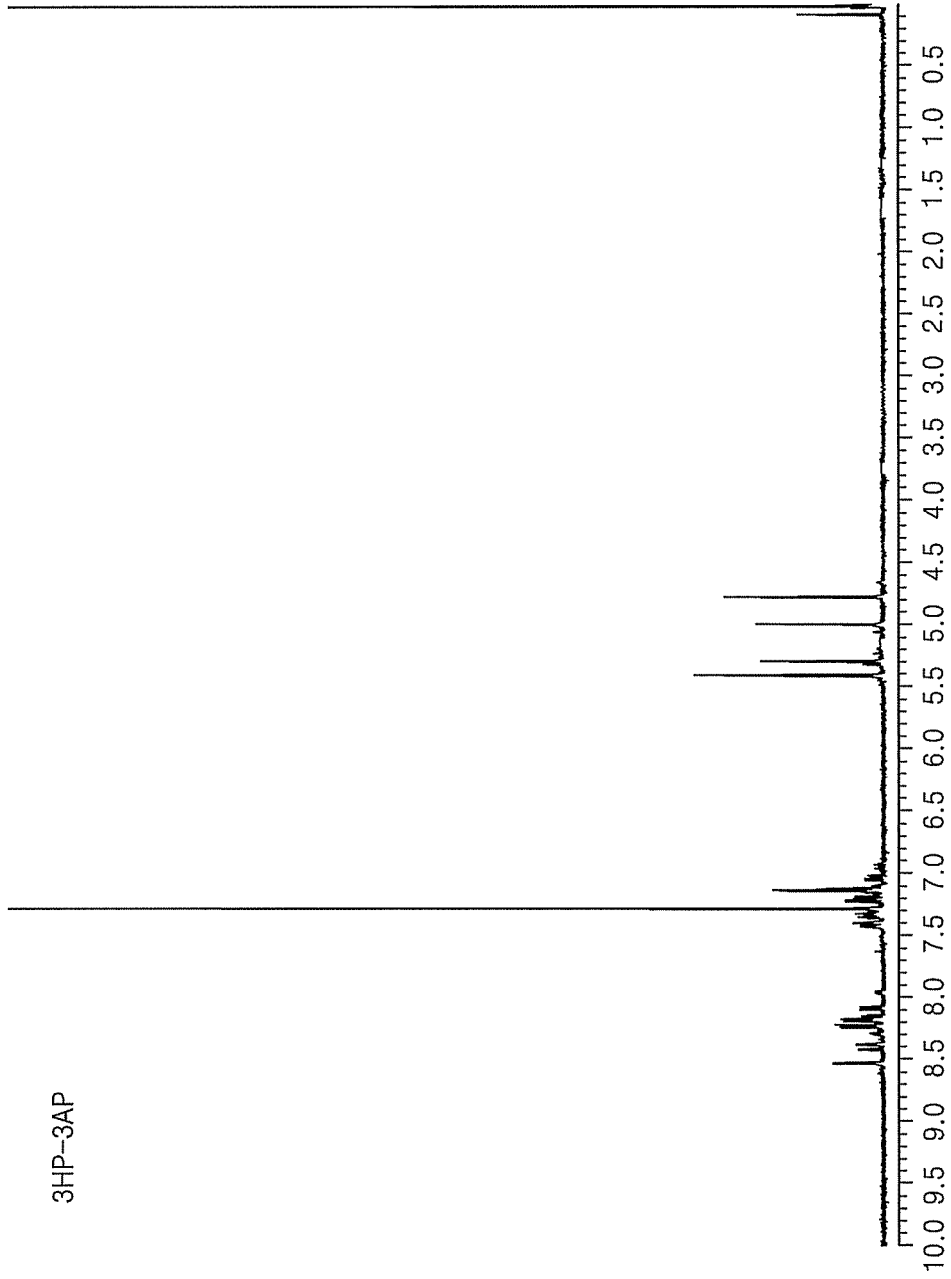
FIG. 2A is a nuclear magnetic resonance (NMR) spectrum of 3HP-3AP, represented by Formula 15, prepared according to Synthesis Example 1.

After washing, the organic layer was dried with MgSO$_4$ and filtered. The residual solution was dried using a rotary evaporator to remove the solvent, and the purified product was dried in a vacuum oven at 40° C. for 6 hours to obtain 3HP-3AP as represented by Formula 15. The structure of 3HP-3AP was identified by the nuclear magnetic resonance (NMR) spectra of FIGS. 2A and 2B.

Synthesis Example 2

Preparation of 8HQD-3AP, represented by Formula 7

10 g (0.063 mol) of 8-hydroxyquinaldine, having the structure below, 4.36 g (0.138 mol) of p-formaldehyde and 6.49 g (0.069 mol) of 3-aminopyridine were added to a 100 ml one-neck round-bottom flask and mixed while held in an oil bath at 90° C.

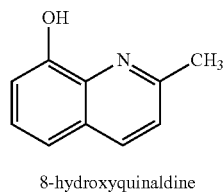

8-hydroxyquinaldine

After about 30 minutes, when the initially opaque mixture became a yellow transparent gel type material, the reaction was quenched using chloroform, and then the mixture was cooled to room temperature. The cooled crude product was base-washed twice through solvent extraction using a 1N NaOH aqueous solution, and washed once with deionized water.

Figure 3A:
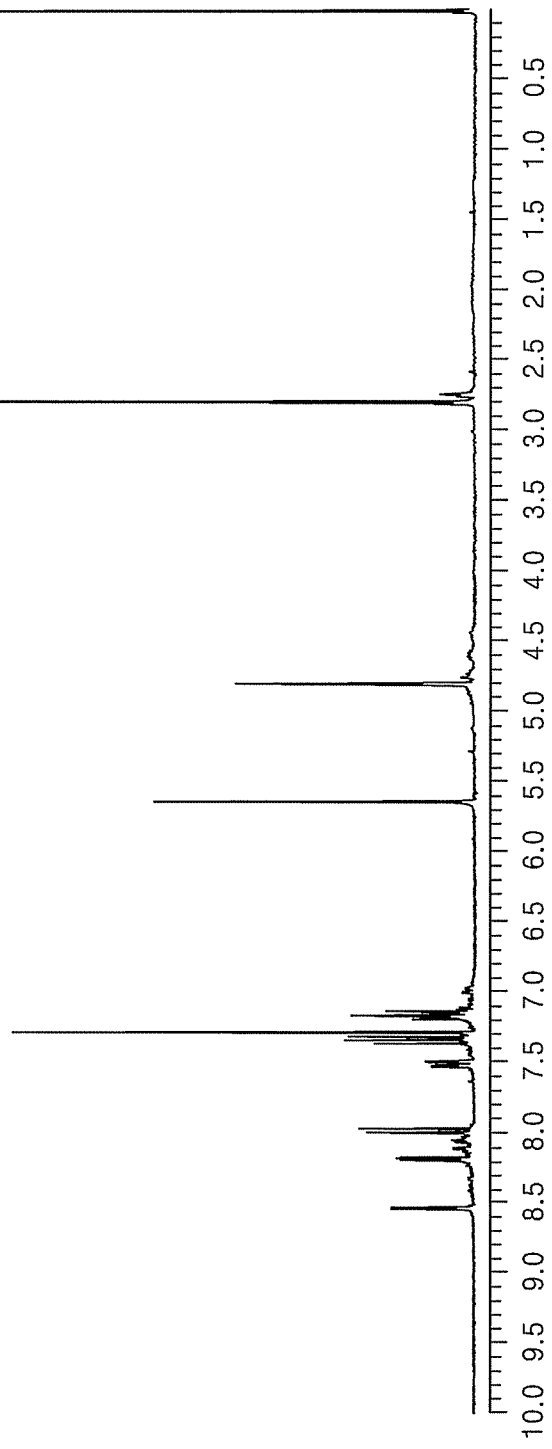
FIG. 3A is a nuclear magnetic resonance (NMR) spectrum of 8HQD-3AP, represented by Formula 7, prepared according to Synthesis Example 2.
Figure 3B:
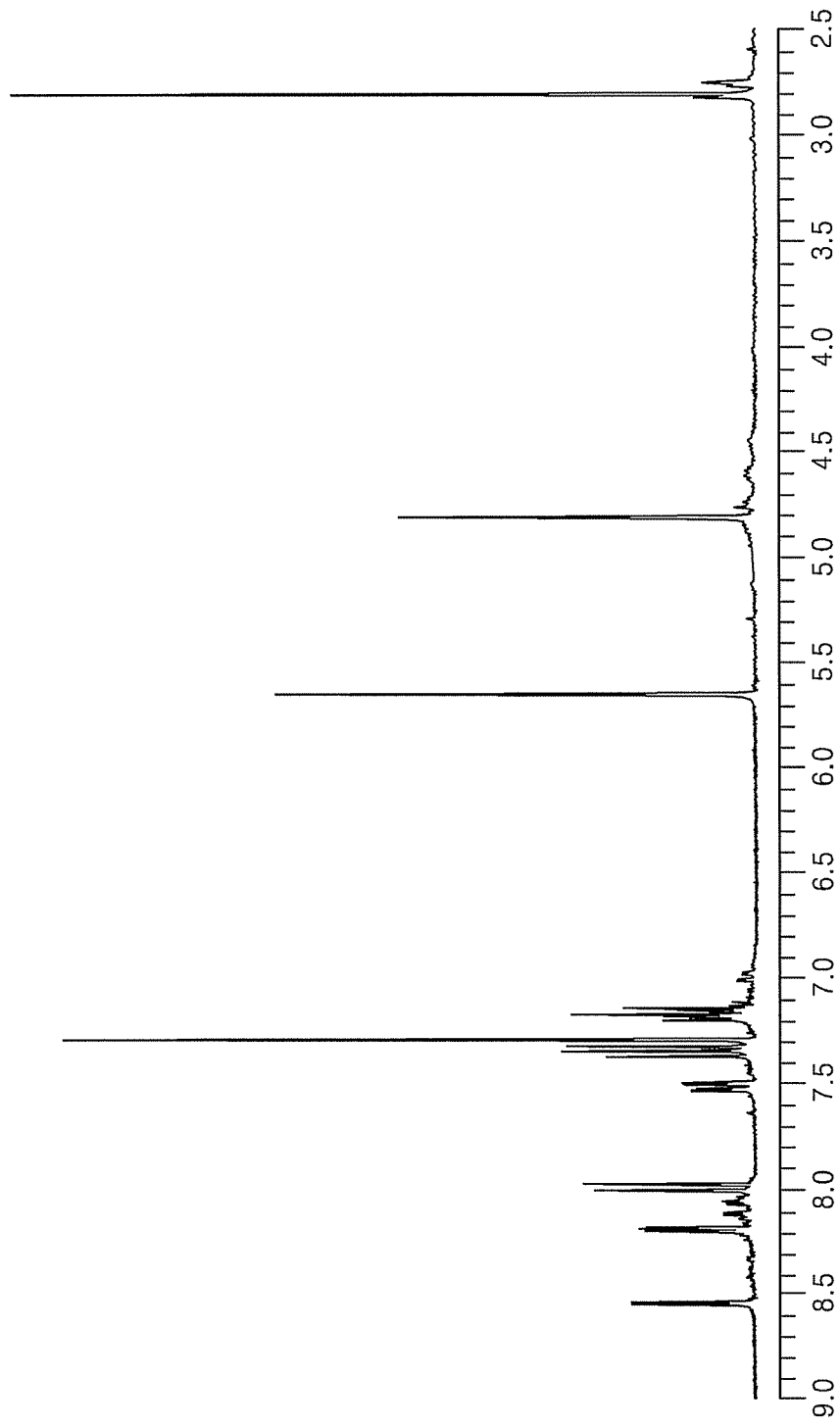
FIG. 3B is an expanded portion of FIG. 3A.

After washing, the organic layer was dried with $MgSO_4$ and filtered. The residual solution was dried using a rotary evaporator to remove the solvent, and the purified product was dried in a vacuum oven at 40° C. for 6 hours to obtain 8HQD-3AP, represented by Formula 7. The structure of 8HQD-3AP was identified by the nuclear magnetic resonance (NMR) spectra of FIGS. 3A and 3B.

Synthesis Example 3

Preparation of 8HP-2AP, represented by Formula 14

10 g (0.069 mol) of 8-hydroxyquinoline, 4.81 g (0.152 mol) p-formaldehyde and 7.23 g (0.076 mol) of 2-aminopyridine were added to a 100 ml one-neck round-bottom flask and mixed while held in an oil bath at 90° C.

After about 30 minutes, when the initially opaque mixture became a yellow transparent gel type material, the reaction was quenched using chloroform, and then the mixture was cooled to room temperature. The cooled crude product was base-washed twice through solvent extraction using a 1N NaOH aqueous solution, and washed once with deionized water.

After washing, the organic layer was dried with $MgSO_4$ and filtered. The residual solution was dried using a rotary evaporator to remove the solvent, and the purified product was dried in a vacuum oven at 40° C. for 6 hours to obtain 8HP-2AP, represented by Formula 14. As a result of identifying the structure of the compound by an NMR spectrum, peaks illustrating characteristics of a benzoxazine ring were observed at chemical shifts of 5.6 ppm and 4.8 ppm as shown in FIGS. 2A, 2B, 3A and 3B.

Synthesis Example 4

Preparation of a polymer of 3HP-3AP, represented by Formula 15, and PBI 65 parts by weight of 3HP-3AP, represented by Formula 15 and prepared in Synthesis Example 1, was blended with 35 parts by weight of polybenzimidazole, and the mixture was cured at a temperature in the range of about 180 to 240° C. to obtain a polymer of 3HP-3AP, represented by Formula 15, and PBI.

Figure 4:
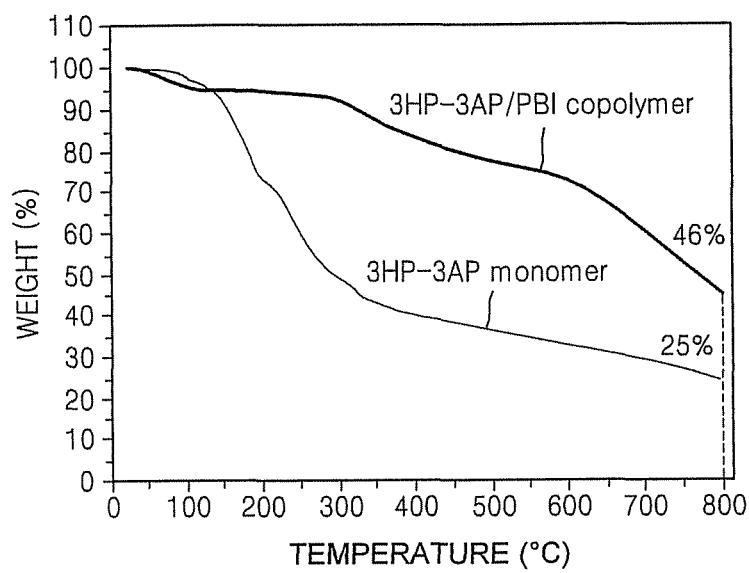
FIG. 4 is a graph illustrating the results of a thermogravimetric analysis of 3HP-3AP, represented by Formula 15, prepared according to Synthesis Example 1 and the polymer of 3HP-3AP, represented by Formula 15, and PBI prepared according to Synthesis Example 4.

The thermal stability of 3HP-3AP, represented by Formula 15 prepared in Synthesis Example 1, and the polymer of 3HP-3AP, represented by Formula 15 and PBI prepared in Synthesis Example 4, were measured using thermogravimetric analysis, and the results are shown in FIG. 4. The thermal weight loss was measured at 800° C. in FIG. 4. Referring to FIG. 4, the polymer of 3HP-3AP and PBI had higher thermal stability compared to the 3HP-3AP monomer.

Figure 9:
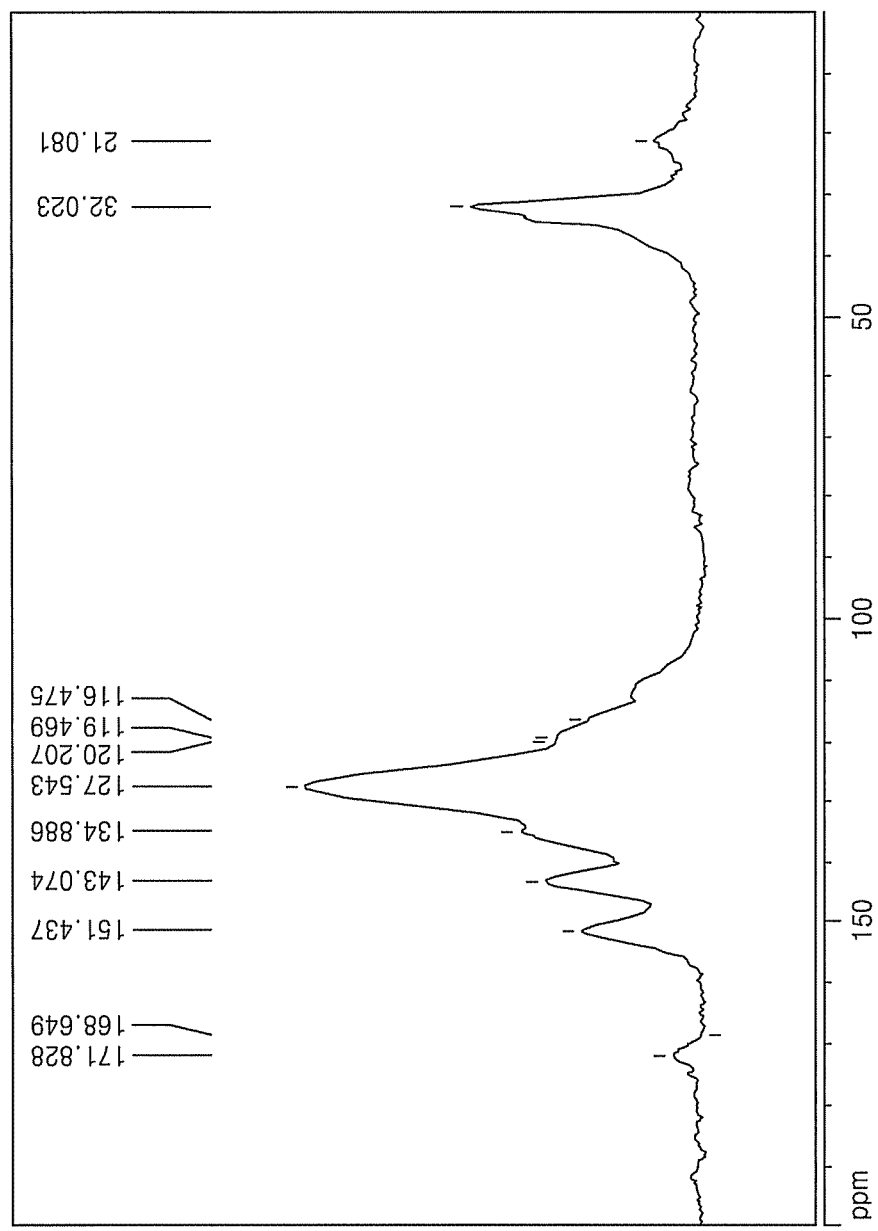
FIG. 9 is a graph illustrating a solid nuclear magnetic resonance (NMR) spectrum of a solid-phase polymer of 3HP-3AP, represented by Formula 15, and PBI prepared according to Synthesis Example 4 of the present invention.

The structure of the solid-phase polymer of 3HP-3AP, represented by Formula 15 and PBI prepared in Synthesis Example 4, was identified by a solid nuclear magnetic resonance (NMR) spectrum, and the results are shown in FIG. 9. The NMR was performed using a Varian Unity INOVA600 at 600 MHz.

Example 1

Preparation of an Electrode for a Fuel Cell and a Fuel Cell Using the Electrode 1 g of a catalyst, in which 50% by weight of PtCo is supported on carbon, and 3 g of NMP as a solvent were added to a container, and the mixture was agitated using a mortar to prepare a slurry. A solution of 3% by weight of 3HP-3AP, represented by Formula 15 prepared according to Synthesis Example 1, and NMP was added to the slurry and stirred to prepare 0.025 g of the compound represented by Formula 15.

Then, a solution of 5% by weight of polyvinylidenefluoride and NMP was added to the mixture to set the amount of the polyvinylidenefluoride to 0.025 g, and the mixture was stirred for 10 minutes to prepare a slurry for a cathode catalyst layer. Carbon paper was cut into pieces of 47 $cm^2$ in size, and the pieces were fixed on a glass plate and coated using a doctor blade (Sheen instrument), wherein the gap interval of the doctor blade was 600 μm. The slurry for a cathode catalyst layer was coated on the carbon paper and dried at room temperature for 1 hour, at 80° C. for 1 hour, at 120° C. for 30 minutes and at 150° C. for 15 minutes to prepare a cathode (a fuel electrode). The amount of loaded Pt/Co in the prepared cathode was 3.0 $mg/cm^2$.

An electrode prepared according to the following process was used as an anode. 2 g of a catalyst in which 50% by weight of Pt is supported on carbon and 9 g of NMP solvent were added to a container and the mixture was agitated in a high-speed agitator for 2 minutes.

Then, a solution of 0.05 g of polyvinylidenefluoride dissolved in 1 g of NMP was added thereto and agitated for 2 minutes to prepare a slurry for an anode catalyst layer. The slurry was coated on carbon paper on which a microporous layer had been coated, using a bar coater. The amount of loaded Pt in the prepared anode was 1.4 $mg/cm^2$.

65 parts by weight of benzoxazine-based monomer, represented by the formula below, and 35 parts by weight of polybenzimidazole were blended, and cured at a temperature in the range of 180 to 240° C.

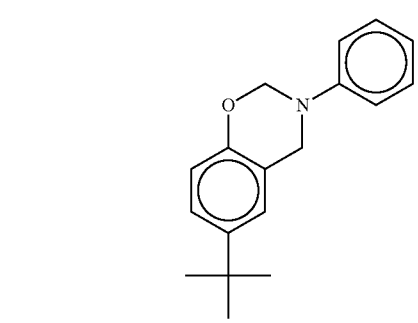

Then, to prepare an electrolyte membrane, the resultant was impregnated with 85% by weight of phosphoric acid at 80° C. for longer than 4 hours. Here, the amount of phosphoric acid was about 450 parts by weight based on 100 parts by weight of electrolyte membrane. The amount of loaded Pt/Co in the prepared cathode was about 2.17 mg/cm$^2$, and the amount of loaded Pt in the prepared anode was 1.5 mg/cm$^2$.

A membrane electrode assembly (MEA) was prepared by interposing the electrolyte membrane between the cathode and the anode. Here, the cathode and anode were not impregnated with phosphoric acid.

A 200 μm PTFE membrane for a main gasket and a 20 μm PTFE membrane for a sub gasket were overlapped on an interface between the electrodes and electrolyte membrane in order to prevent gas permeation between the cathode and the anode. In order to assemble a cell, the pressure applied to the MEA was adjusted to 1, 2, 3 N-m Torque, step by step, using a wrench.

Characteristics of fuel cells were measured while operating by supplying hydrogen to the anode at 100 ccm and supplying air to the cathode at 250 ccm at 150° C. while the electrolyte membrane was not hydrated. Since cell efficiency increases with time by using the electrolyte doped with phosphoric acid, the final efficiency was measured after the fuel cell was activated and was performed until the operational voltage was maximized. The area of the cathode and the anode was fixed to 2.8 2.8=7.84 cm$^2$, and the thickness of the cathode was about 430 μm and the thickness of the anode was about 390 μm, although the thicknesses of the cathode and the anode may vary according to the distribution of thickness of the carbon paper.

Example 2

Preparation of an Electrode for a Fuel Cell and a Fuel Cell Using the Electrode A cathode and a fuel cell using the cathode were prepared in the same manner as in Example 1, except that 8HP-2AP, represented by Formula 14 prepared according to Synthesis Example 2, was used instead of 3HP-3AP, represented by Formula 15, in the preparation of the cathode.

Example 3

Preparation of an Electrode for a Fuel Cell and a Fuel Cell Using the Electrode A cathode and a fuel cell using the cathode were prepared in the same manner as in Example 1, except that 8HQD-3AP, represented by Formula 7 prepared according to Synthesis Example 3, was used instead of 3HP-3AP, represented by Formula 15, in the preparation of the cathode.

Comparative Example 1

Preparation of an Electrode for a Fuel Cell and a Fuel Cell Using the Electrode A cathode and a fuel cell using the cathode were prepared in the same manner as in Example 1, except that 3HP-3AP, represented by Formula 15, was not added in the preparation of the cathode.

In addition, cell potential changes as a function of current density were measured in fuel cells prepared according to Example 1 and Comparative Example 1, and the results are shown in FIG. 1. The d1, d3, d5 and d7 of FIG. 1 respectively indicate first day, third day, fifth day and seventh day. Referring to FIG. 1, high potentials of fuel cells can be maintained with the passage of time.

The performance of fuel cells prepared according to Examples 1 to 3 and Comparative Example 1 was tested and the results are shown in Table 1.

TABLE 1

| | Voltage at 0.3 A/cm$^2$ (V) | Tafel's slope (mV/sec) | Time taken to reach 95% of the maximum voltage (hr) |
|---|---|---|---|
| Compound of Formula 14 (Example 2) | 0.667 | 75 | 60 |
| Compound of Formula 7 (Example 3) | 0.657 | 79 | 80 |
| Compound of Formula 15 (Example 1) | 0.671 | 95 | 100 |
| Comparative Example 1 | 0.678-0.692 | 97-100 | 100 |

According to Table 1, the voltage characteristics of fuel cells of Examples 1 to 3, which include an additive having high affinity for phosphoric acid, were improved compared to that of Comparative Example 1, since reduction in the reactivity of the oxygen/reduction reaction (ORR) due to phosphoric acid was inhibited.

As shown in Table 1, the Tafel's slopes of Examples 1 to 3 are lower than that of Comparative Example 1, and thus it can be seen that the ORR mechanism was changed. In addition, the fuel cells of Examples 1 to 3 can reach the maximum voltage more quickly than the fuel cell of Comparative Example 1 since t fuel cells of Examples 1 to 3 have excellent affinity to phosphoric acid.

Example 4

Preparation of an Electrolyte Membrane for a Fuel Cell and a Fuel Cell Using the Electrolyte Membrane 1 g of a catalyst in which 50% by weight of PtCo is loaded on carbon and 3 g of NMP as a solvent were added to a container, and the mixture was agitated using a mortar to prepare a slurry. Then, a solution of 5% by weight of polyvinylidenefluoride and NMP was added to the mixture to set the amount of the polyvinylidenefluoride to 0.025 g, and the mixture was stirred for 10 minutes to prepare a slurry for a cathode catalyst layer.

Carbon paper was cut into pieces of 47 cm$^2$ in size, and the pieces were fixed on a glass plate and coated using a doctor blade (Sheen instrument), wherein the gap interval of the doctor blade was 600 The slurry for a cathode catalyst layer was coated on the carbon paper and dried at room temperature for 1 hour, at 80° C. for 1 hour, at 120° C. for 30 minutes and at 150° C. for 15 minutes to prepare a cathode (a fuel electrode). The amount of loaded Pt/Co in the prepared cathode was 3.0 mg/cm$^2$.

An electrode prepared according to the following process was used as an anode. 2 g of a catalyst in which 50% by weight of Pt is supported on carbon and 9 g of NMP solvent were added to a container and the mixture was agitated in a high-speed agitator for 2 minutes. Then, a solution of 0.05 g of polyvinylidenefluoride dissolved in 1 g of NMP was added thereto and agitated for 2 minutes to prepare a slurry for an anode catalyst layer. The slurry was coated on carbon paper on which a microporous layer had been coated, using a bar coater. The amount of loaded Pt in the prepared anode was 1.4 mg/cm².

65 parts by weight of 3HP-3AP represented by Formula 15 prepared in Synthesis Example 1 was blended with 35 parts by weight of PBI, and the mixture was cured at about 220° C.

Then, the resultant was impregnated with 85% by weight of phosphoric acid at 80° C. for longer than 4 hours to prepare an electrolyte membrane. Here, the amount of phosphoric acid was about 530 parts by weight based on 100 parts by weight of electrolyte membrane.

A membrane electrode assembly (MEA) was prepared by interposing the electrolyte membrane between the cathode and the anode. Here, the cathode and anode were not impregnated with phosphoric acid.

A 200 μm PTFE membrane for a main gasket and a 20 μm PTFE membrane for a sub gasket were overlapped on an interface between the electrodes and electrolyte membrane in order to prevent gas permeation, between the cathode and the anode. In order to assemble a cell, pressure applied to the MEA was adjusted, step by step, to 1, 2, 3 N-m Torque using a wrench.

Characteristics of fuel cells were measured while operating by supplying hydrogen to the anode at 100 ccm and supplying air to the cathode at 250 ccm at 150° C. while the electrolyte membrane was not hydrated. Since cell efficiency increases with time by using the electrolyte doped with phosphoric acid, the final efficiency was measured after the fuel cell had aged until the operational voltage reached a maximum. The area of the cathode and the anode is fixed to 2.8 2.8=7.84 cm², and the thickness of the cathode was about 430 μm and the thickness of the anode was about 390 μm, although the thicknesses of the cathode and the anode may vary according to the distribution of thicknesses of the carbon paper.

Figure 5:
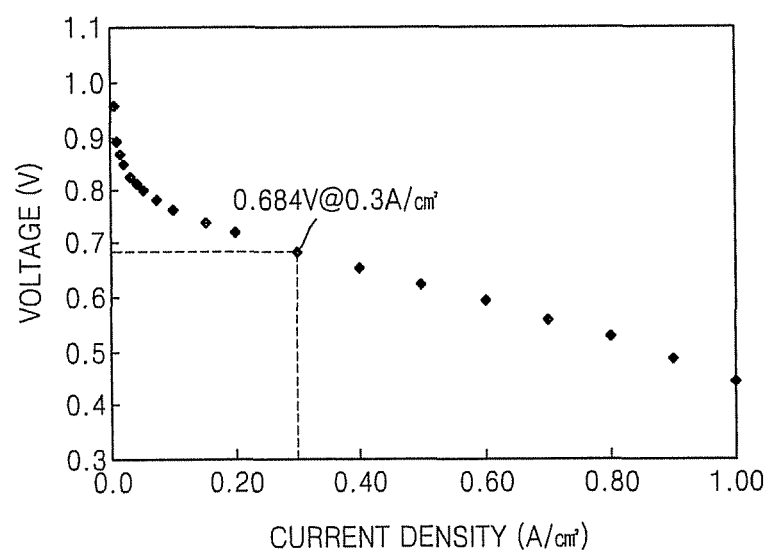
FIG. 5 is a graph illustrating voltage with respect to current density of a fuel cell prepared according to Example 4 of the present invention.

The voltage as a function of current density of the fuel cell prepared according to Example 4 was measured, and the results are shown in FIG. 5. Referring to FIG. 5, the fuel cell of Example 4 had an open circuit voltage (OCV) of 1.05 V as well as a voltage of 0.684 V at 0.3 A/cm².

Figure 6:
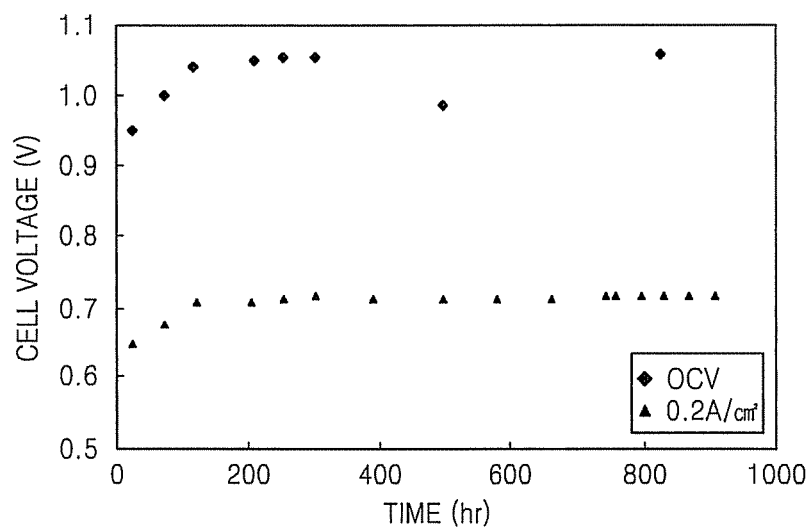
FIG. 6 is a graph illustrating cell voltage over time of a fuel cell prepared according to Example 4 of the present invention.

Furthermore, the cell voltage over time of the fuel cell of Example 4 was measured, and the results are shown in FIG. 6. In FIG. 6, "♦ OCV" denotes an open circuit voltage (OCV), and "▲ 0.2 A/cm²" denotes cell voltage at a current density of 0.2 A/cm². Referring to FIG. 6, it can be seen that the fuel cell of Example 4 has excellent cell voltage characteristics.

Example 5

Preparation of an Electrolyte Membrane for a Fuel Cell and a Fuel Cell Using the Electrolyte Membrane An electrolyte membrane and a fuel cell using the electrolyte membrane were prepared in the same manner as in Example 4, except that 8HQD-3AP, represented by Formula 7, was used instead of 3HP-3AP, represented by Formula 15, in the formation of the electrolyte membrane.

Figure 7:
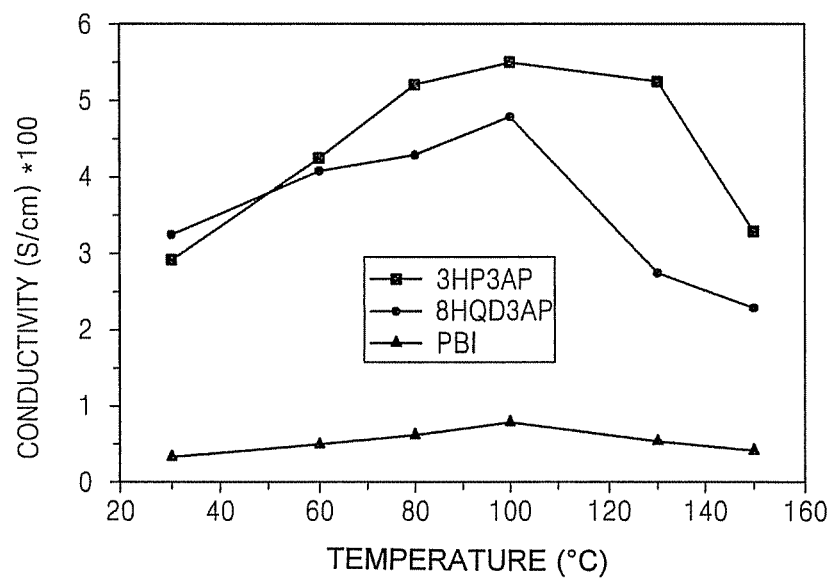
FIG. 7 is a graph illustrating conductivity with respect to temperature of electrolyte membranes prepared according to Examples 4 and 5 of the present invention.
Figure 8:
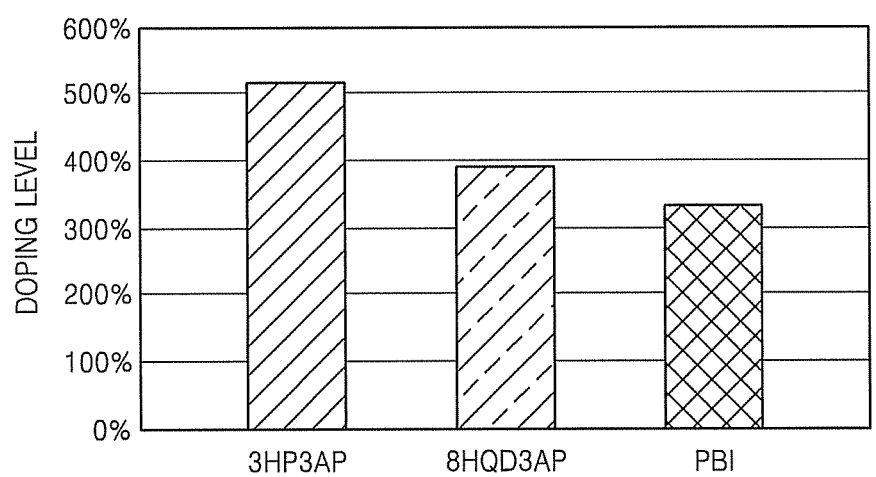
FIG. 8 is a graph illustrating the phosphoric acid doping level of electrolyte membranes prepared according to Examples 4 and 5 of the present invention.

The conductivity as functions of temperature and phosphoric acid doping level of the electrolyte membrane prepared in Examples 4 and 5 were measured, and the results are shown in FIGS. 7 and 8. Referring to FIGS. 7 and 8, the electrolyte membrane of Examples 4 and 5 has higher conductivity when compared with the PBI electrolyte membrane. In FIG. 8, the doping level is shown in percentages based on the weight of the impregnated amount of phosphoric acid.

Example 6

Preparation of a Fuel Cell

A fuel cell was prepared in the same manner as in Example 4, except that 3HP-3AP, represented by Formula 15, was used in the preparation of the cathode.

Comparative Example 2

Preparation of a Fuel Cell

A fuel cell was prepared in the same manner as in Example 6, except that PBI electrolyte membrane was used instead of 3HP-3AP, represented by Formula 15, in the preparation of the cathode and 3HP-3AP, represented by Formula 15, was not added in the preparation of the cathode.

Figure 10:
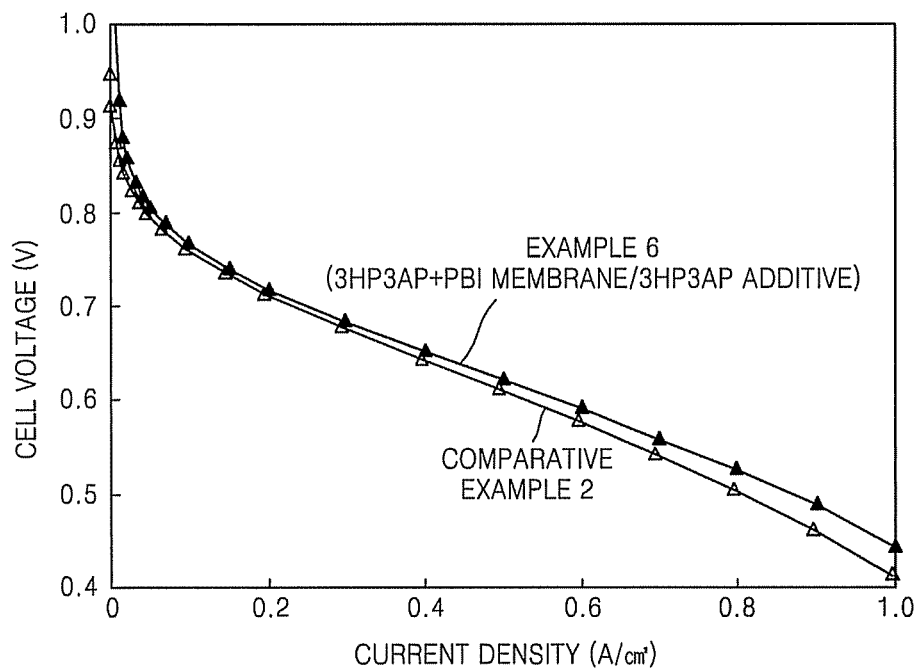
FIG. 10 is a graph illustrating cell voltage with respect to current density of fuel cells prepared according to Example 6 and Comparative Example 2 of the present invention.

Cell voltage characteristics with respect to the current density of fuel cells prepared in Example 6 and Comparative Example 2 were measured, and the results are shown in FIG. 10. Referring to FIG. 10, the performance of the MEA prepared in Example 6 was improved compared with that of the MEA prepared in Comparative Example 2.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:
1. An electrode for a fuel cell comprising a monomer selected from the group consisting of Formulae 2 through 21 or a polymer of the monomer:

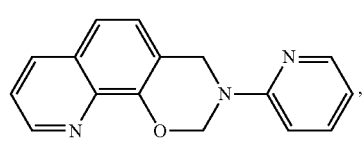

Formula 2

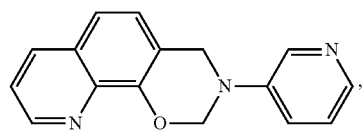

Formula 3

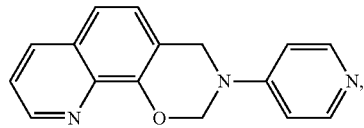

Formula 4

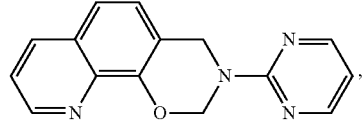

Formula 5

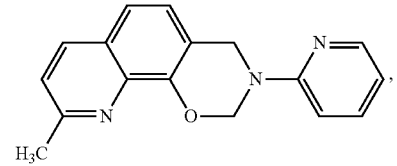

Formula 6

Formula 7
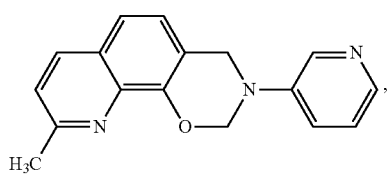
Formula 8
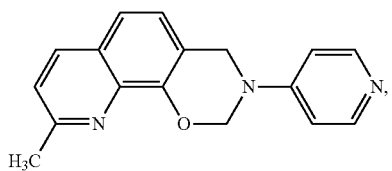
Formula 9
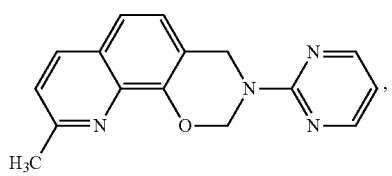
Formula 10
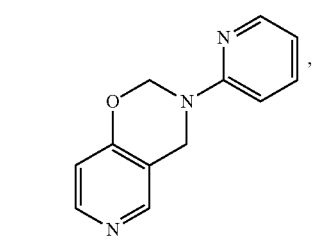
Formula 11
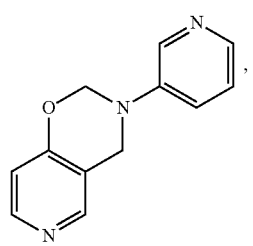
Formula 12
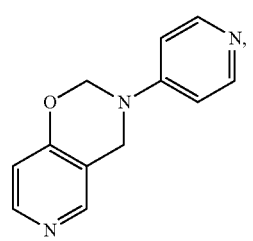
Formula 13
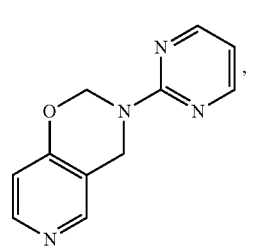
Formula 14
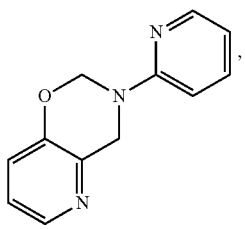
Formula 15
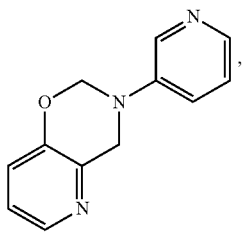
Formula 16
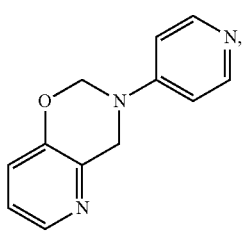
Formula 17
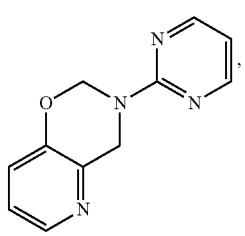
Formula 18
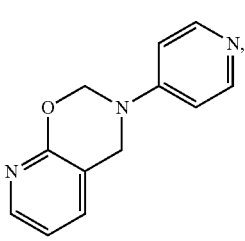
Formula 19
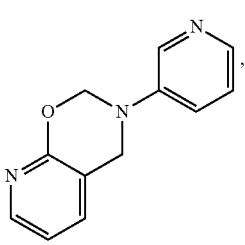
Formula 20
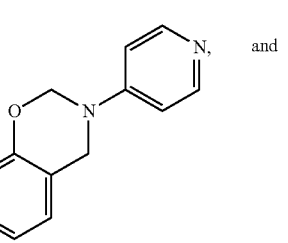

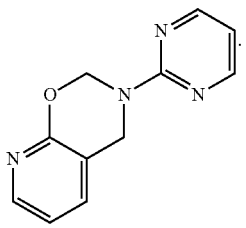

Formula 21

2. The electrode of claim 1, wherein the polymer is a polymerization product of the monomer or a polymerization product of the monomer and a crosslinkable compound.

3. The electrode of claim 2, further comprising a catalyst layer comprising a catalyst.

4. The electrode of claim 3, wherein the amount of the polymer of the monomer is in the range of 0.1 to 65 parts by weight based on 100 parts by weight of the catalyst.

5. The electrode of claim 3, wherein the catalyst is

Pt, a metal-Pt alloy including Pt and at least one metal selected from the group consisting of Au, Pd, Rh, Ir, Ru, Sn, Mo, Co, and Cr, or a mixture including Pt and at least one metal selected from the group consisting of Au, Pd, Rh, Ir, Ru, Sn, Mo, Co, and Cr.

6. The electrode of claim 3, wherein the catalyst is a catalyst metal or a support catalyst in which the catalyst metal is loaded on a carbonaceous support, and the catalyst metal is Pt, a metal-Pt alloy including Pt and at least one metal selected from the group consisting of Au, Pd, Rh, Ir, Ru, Sn, Mo, Co, and Cr, or a mixture including Pt and at least one metal selected from the group consisting of Pt, Au, Pd, Rh, Ir, Ru, Sn, Mo, Co, and Cr.

7. The electrode of claim 3, wherein the catalyst layer further comprises at least one proton conductor selected from the group consisting of phosphoric acid and a C1-C20 organic phosphonic acid.

8. The electrode of claim 3, wherein the catalyst layer further comprises a catalyst and a binder, the binder is at least one polymer selected from the group consisting of poly(vinylidene fluoride), polytetrafluoroethylene (PTFE), a tetrafluoroethylene-hexafuoroethylene copolymer, fluorinated ethylene propylene (FEP), styrene butadiene rubber (SBR) and polyurethane, and the concentration of the binder is in the range of 0.1 to 50 parts by weight based on 100 parts by weight of the catalyst.

9. The electrode of claim 2 further comprising at least one binder selected from the group consisting of poly(vinylidene fluoride), polytetrafluoroethylene (PTFE), a tetrafluoroethylene-hexafuoroethylene copolymer, fluorinated ethylene propylene (FEP), styrene butadiene rubber (SBR) and polyurethane.

10. An electrolyte membrane for a fuel cell comprising a polymer comprising a monomer selected from the group consisting of Formulae 2 through 21:

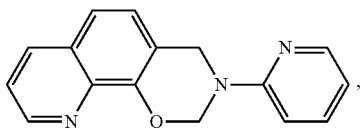
Formula 2

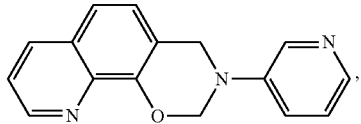
Formula 3

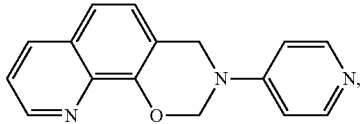
Formula 4

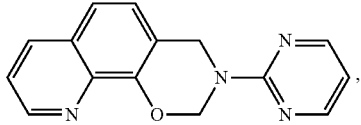
Formula 5

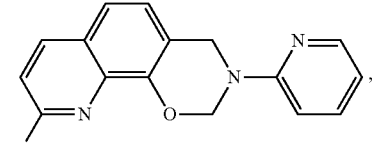
Formula 6

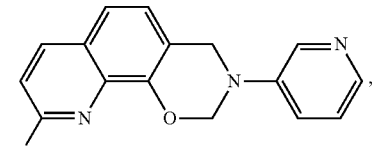
Formula 7

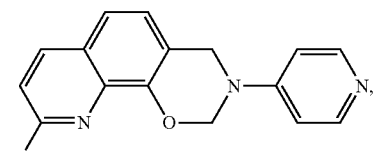
Formula 8

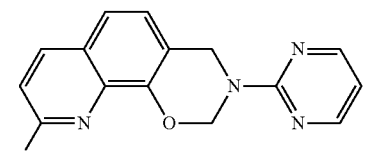
Formula 9

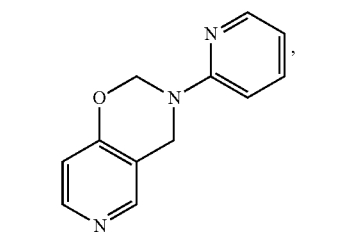
Formula 10

Formula 11 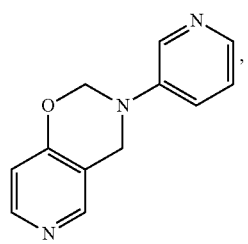

Formula 12 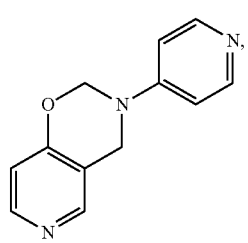

Formula 13 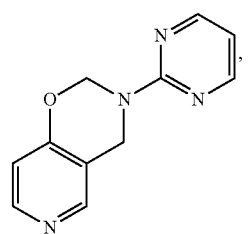

Formula 14 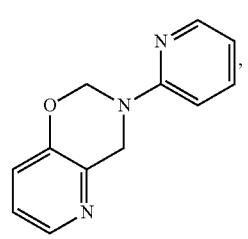

Formula 15 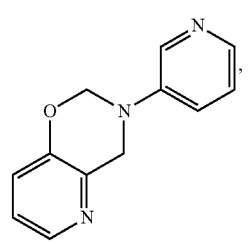

Formula 16 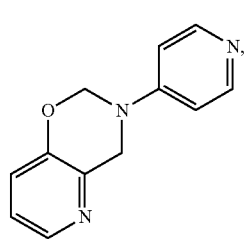

Formula 17 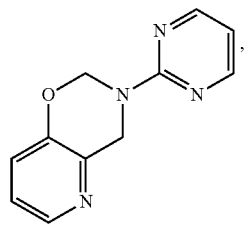

Formula 18 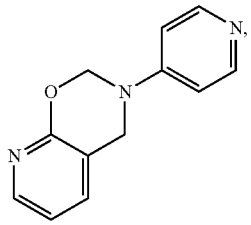

Formula 19 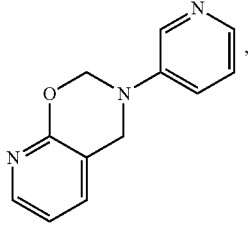

Formula 20 and 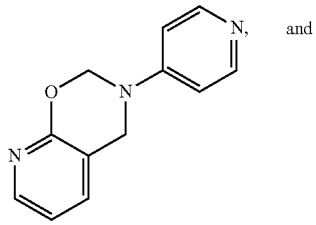

Formula 21 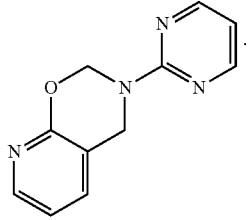

11. The electrolyte membrane of claim 10, further comprising at least one proton conductor selected from the group consisting of phosphoric acid and a C1-C20 organic phosphonic acid.

12. A fuel cell comprising:
a cathode;
an anode; and
an electrolyte membrane interposed between the cathode and the anode,
wherein at least one of the cathode and the anode comprises the electrode according to claim 1 which comprises a monomer selected from the group consisting of Formulae 2 through 21 or a polymer of the monomer.

13. The fuel cell of claim 12, wherein the electrolyte membrane comprises a polymer of the monomer or a polymerization product of the monomer and a crosslinkable compound.

* * * * *